(12) United States Patent
Mirzaei et al.

(10) Patent No.: US 12,316,159 B2
(45) Date of Patent: May 27, 2025

(54) METHODS AND SYSTEMS FOR POWER SUPPLY

(71) Applicant: GE Precision Healthcare LLC, Wauwatosa, WI (US)

(72) Inventors: Saeid Mirzaei, Muskego, WI (US); Benarji Reddycherla Varma, Sussex, WI (US); Prajjwal Dhungana, Germantown, WI (US); Joseph Marco, Fox Point, WI (US)

(73) Assignee: GE Precision Healthcare LLC, Wauwatosa, WI (US)

( * ) Notice: Subject to any disclaimer, the term of this patent is extended or adjusted under 35 U.S.C. 154(b) by 170 days.

(21) Appl. No.: 17/854,544

(22) Filed: Jun. 30, 2022

(65) Prior Publication Data

US 2022/0393503 A1 Dec. 8, 2022

Related U.S. Application Data

(63) Continuation-in-part of application No. 17/341,259, filed on Jun. 7, 2021, now Pat. No. 11,818,827.

(51) Int. Cl.
*H02J 9/06* (2006.01)

(52) U.S. Cl.
CPC .............. *H02J 9/062* (2013.01); *H02J 9/061* (2013.01)

(58) Field of Classification Search
CPC ... H02J 9/062; H02J 9/061; H02J 9/06; A61B 6/4488; A61B 6/481; A61B 6/482; A61B 6/54; A61B 6/032; A61B 6/037; A61B 6/40; A61B 6/56
USPC ....................................................... 307/142
See application file for complete search history.

(56) References Cited

U.S. PATENT DOCUMENTS

| | | | |
|---|---|---|---|
| 2009/0116618 A1* | 5/2009 | Nakayama | A61B 6/035 378/107 |
| 2009/0179496 A1* | 7/2009 | Ho | H02J 9/062 307/66 |
| 2009/0236913 A1* | 9/2009 | Mariasis | H02J 9/062 307/66 |
| 2011/0169333 A1* | 7/2011 | Cohen | H02J 9/062 307/32 |
| 2015/0036786 A1 | 2/2015 | Katcha | |

(Continued)

FOREIGN PATENT DOCUMENTS

| | | | |
|---|---|---|---|
| CN | 114079288 A | | 2/2022 |
| WO | WO2021247278 | * | 9/2021 |

OTHER PUBLICATIONS

EP application 23179711.9 filed Jun. 16, 2023—extended Search Report issued Aug. 23, 2024; 10 pages.

(Continued)

*Primary Examiner* — Elim Ortiz
*Assistant Examiner* — Xuan Ly

(57) ABSTRACT

Various methods and systems are provided for a power supply system. In one example, a method and system includes a power distribution unit (PDU) configured to receive power from a main power source and an uninterruptible power supply (UPS). The UPS includes a timer and the UPS is configured to directly power an output alternating current (AC) load after the main power source in unavailable. The UPS is also configured to power an output high voltage direct current (HVDC) load after the main power source is unavailable for a time delay measured by the timer.

17 Claims, 21 Drawing Sheets

(56) References Cited

U.S. PATENT DOCUMENTS

2018/0263591 A1* 9/2018 Shanthakumar ........ H02J 9/062
2019/0044336 A1 2/2019 Wagner

OTHER PUBLICATIONS

CN 114079288Translation of Abstract, Espacenet Search Result Jul. 1, 2024; 1 page.
EP application 23179711.9 filed Jun. 16, 2023—Partial Search report issued Apr. 11, 2024; 35 pages.
JP application 2023-098163 filed Jun. 15, 2023—Machine Translation of Office Action issued Jun. 5, 2024; 8 pages.
JP application 2023-098163 filed Jun. 15, 2023—Office Action issued Jun. 5, 2024; 6 pages.

* cited by examiner

METHODS AND SYSTEMS FOR POWER SUPPLY

CROSS-REFERENCE TO RELATED APPLICATIONS

This application is a continuation-in-part of and claims priority to U.S. patent application Ser. No. 17/341,259, filed on Jun. 7, 2021, the disclosure of which is incorporated herein by reference in its entirety.

TECHNICAL FIELD

Embodiments of the subject matter disclosed herein relate to providing power to medical imaging system in response to a main power source being absent due to a utility power outage.

BACKGROUND

A computerized tomography (CT) imaging system may receive AC power from a main power source, such as a utility power source. The utility power source may be connected to a utility grid. During some conditions, the main power source may not be provided in response to power outages, component failures or due to the main power source being unexpectedly cut-off.

Certain components within a CT imaging system, such as an X-ray source or X-ray Tube may need to cool down during a shutdown before the main power source is turned off from the CT imaging system. Unexpected power outages may damage certain components, such as an X-ray source or X-ray tube in the CT imaging system. To protect these components and extend their life, it may be desired to provide back-up power during unexpected power outages of the main power source in order to maintain a cool down routine of the components even when the main power source is not available.

SUMMARY

This summary introduces concepts that are described in more detail in the detailed description. It should not be used to identify essential features of the claimed subject matter, nor limit the scope of the claimed subject matter.

In one aspect, a system includes a power distribution unit (PDU) configured to receive power from a main power source and an uninterruptible power supply (UPS). The UPS includes a timer and the UPS is configured to directly power an output alternating current (AC) load after the main power source or supply in unavailable. The UPS is further configured to power an output high voltage direct current (HVDC) load after the main power source is unavailable for a time delay measured by the timer.

In another aspect, a computed tomography (CT) imaging system, includes a gantry coupled to an output HVDC load, a power cabinet coupled to an output AC load, and a power distribution unit (PDU) with a transformer having a primary winding, a first secondary winding, and a second secondary winding. The PDU is configured to receive power from one of a main power source and an uninterruptible power supply (UPS). The CT imaging system also includes a plurality of contactors and a timer coupled to the PDU and UPS, and a controller with computer readable instructions stored on memory thereof for controlling the plurality of contactors based on availability of the main power source and an input from the timer.

In yet another aspect, a method for a computer tomography (CT) imaging system, executed via instructions stored on memory of a controller, includes in response to a main power source being unavailable, powering an output AC load directly via an uninterruptible power supply (UPS), waiting for a time delay, powering an output HVDC load via power coupled from the UPS to a first secondary winding of a transformer, a primary winding of the transformer, a second secondary winding of the transformer, and through a rectifier, and in response to the main power source becoming available determining an X-ray tube condition and powering the output HVDC load via the main power source.

The brief description above is provided to introduce in simplified form a selection of concepts that are further described in the detailed description. It is not meant to identify key or essential features of the claimed subject matter, the scope of which is defined uniquely by the claims that follow the detailed description. Furthermore, the claimed subject matter is not limited to implementations that solve any disadvantages noted above or in any part of this disclosure.

BRIEF DESCRIPTION OF THE DRAWINGS

The present disclosure will be better understood from reading the following description of non-limiting embodiments, with reference to the attached drawings, wherein below.

DETAILED DESCRIPTION

Figure 1:
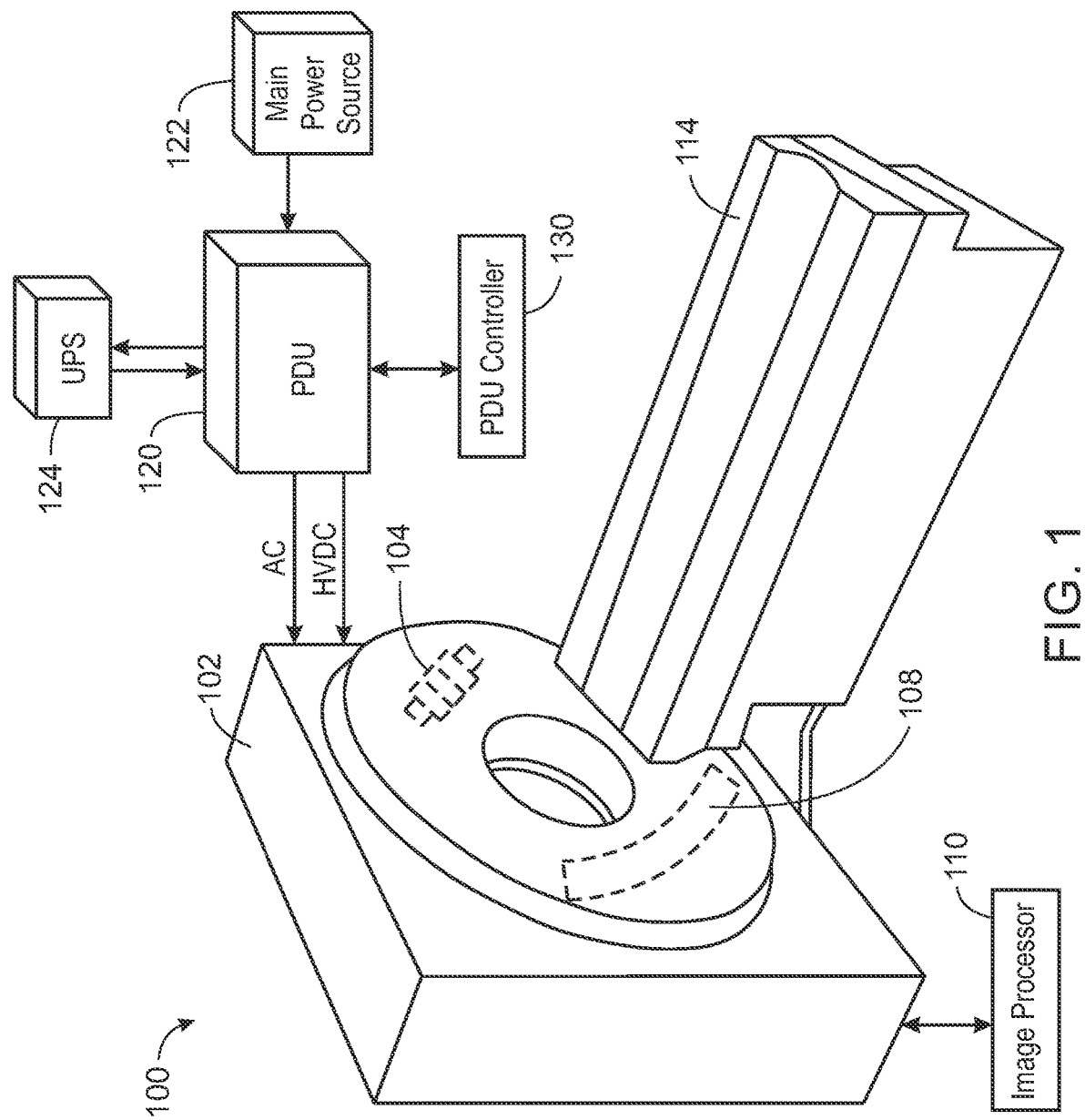
FIG. 1 shows a pictorial view of a computed tomography (CT) imaging system, according to an embodiment.
Figure 2:
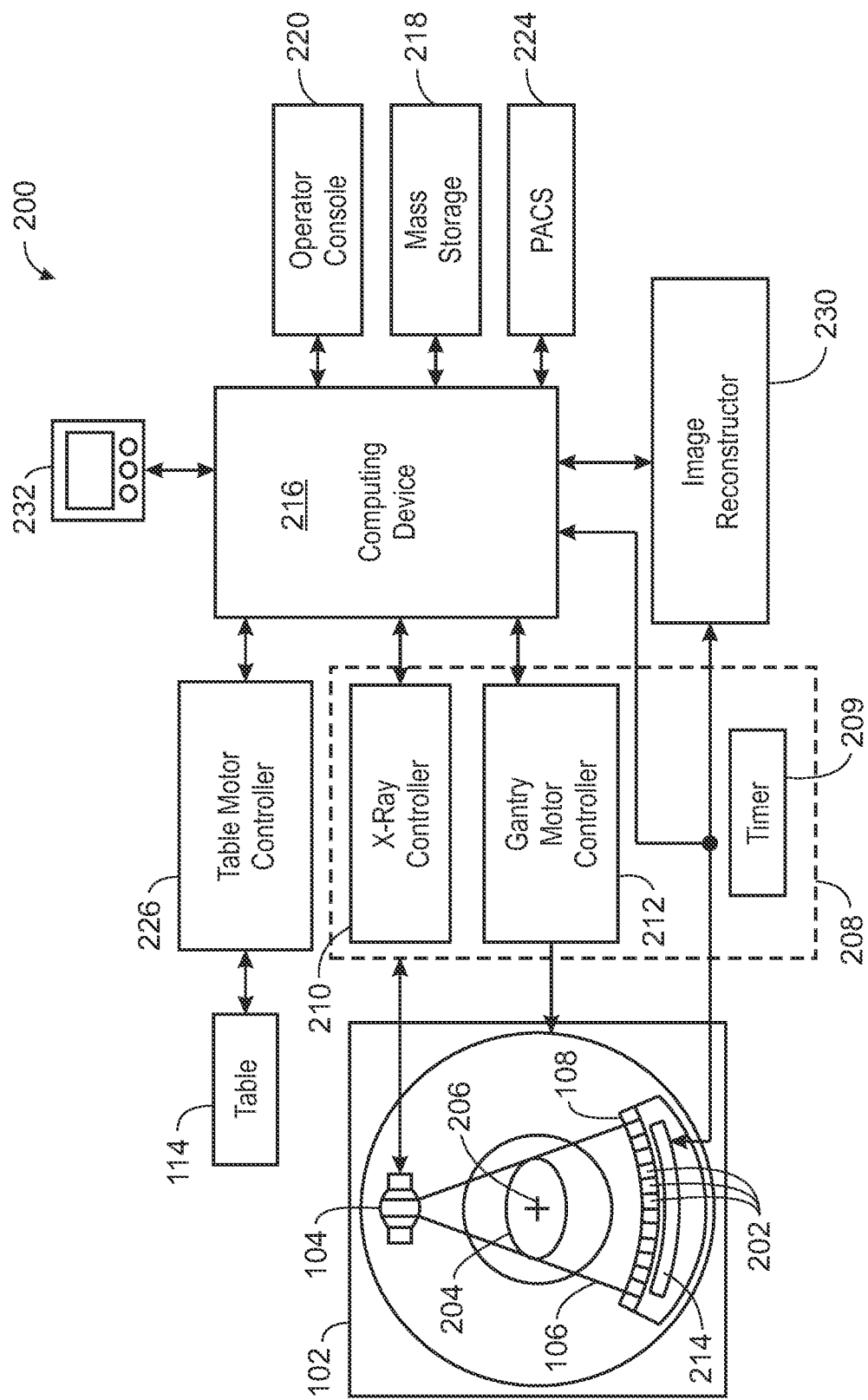
FIG. 2 shows a block diagram of an exemplary CT imaging system, according to an embodiment.
Figure 3:
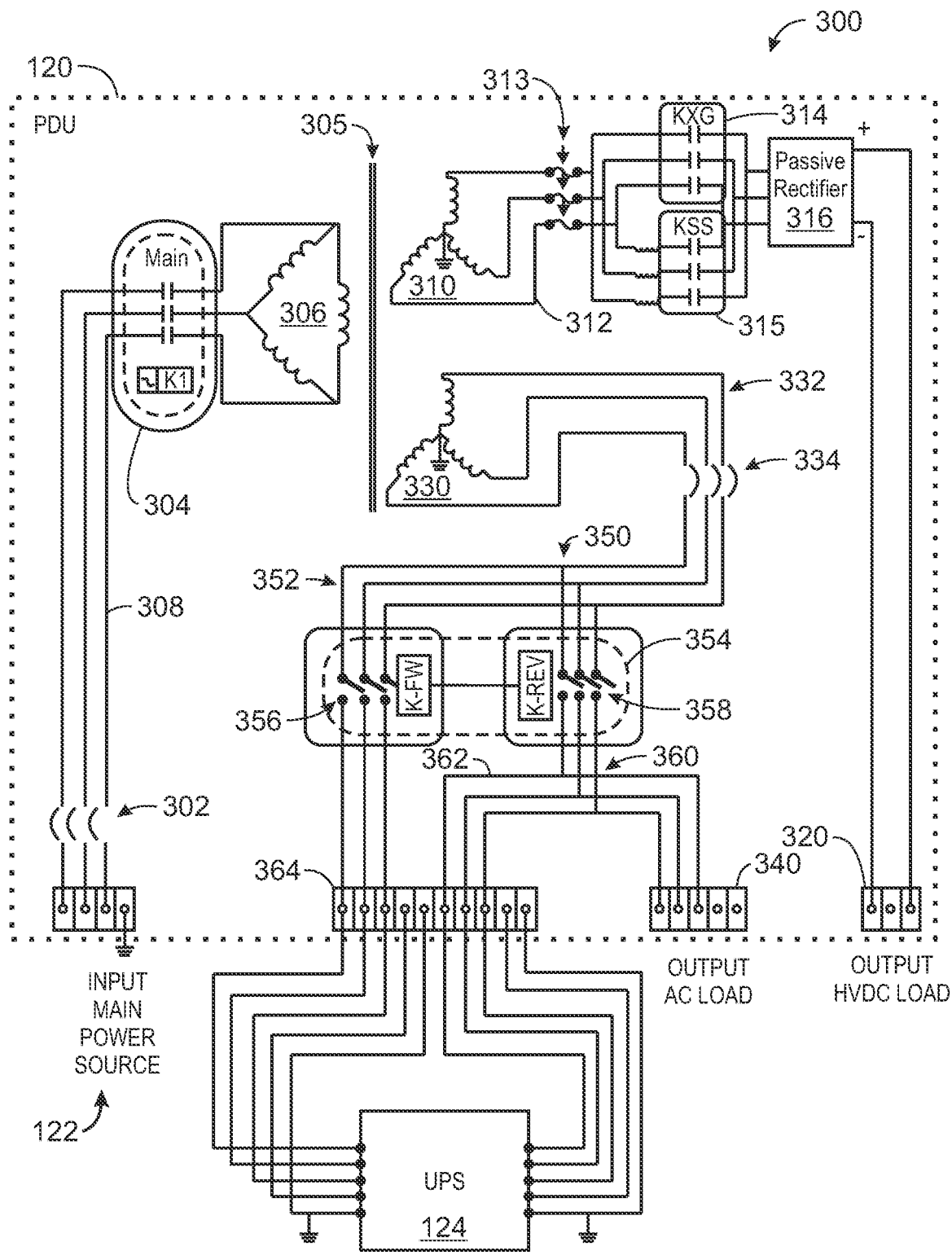
FIG. 3 shows a schematic diagram of an embodiment of power circuitry for powering a CT imaging system.
Figure 4A:
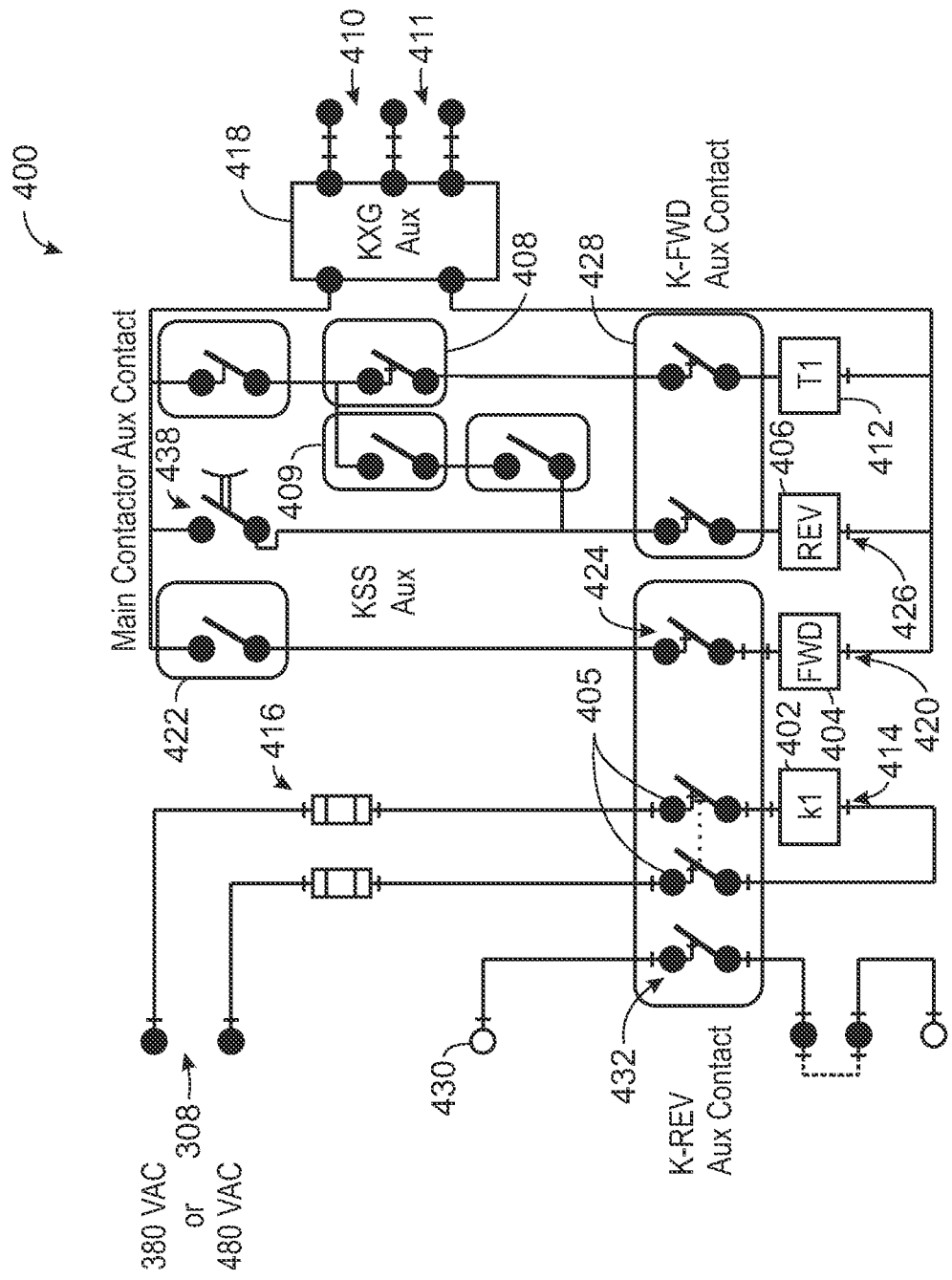
FIGS. 4A and 4B show detailed schematic diagrams of control circuitry for controlling the power circuitry of FIG. 3.
Figure 4B:
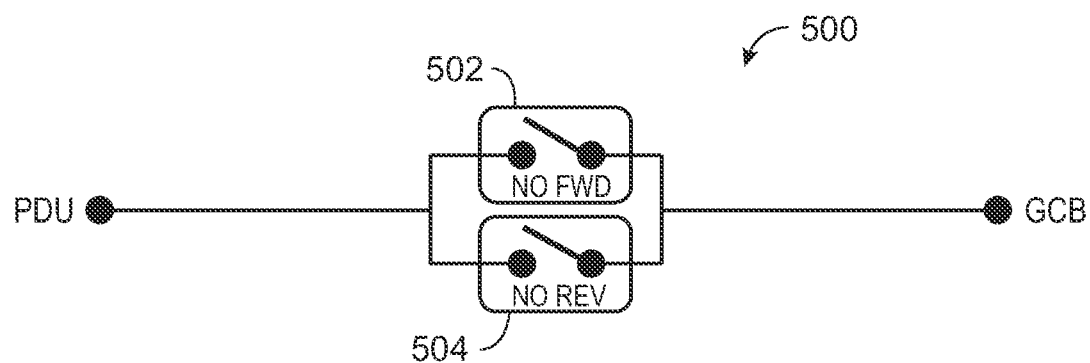

The following description relates to embodiments of a back-up power system for an imaging system, as illustrated in FIGS. 1 and 2. The back-up power system for the imaging system may be configured as an uninterruptible power supply (UPS) coupled to a power distribution unit (PDU) of the imaging system, as shown in FIG. 3. A control circuit of a hot landing switch of the UPS is shown in FIGS. 4A and 4B. FIGS. 5-14B depict the illustration of an electrical circuitry coupling between a main power source or source providing alternating current (AC) power and an uninterruptible power supply (UPS) to a power distribution unit (PDU) in normal operating conditions in power return conditions and the control circuit for the hot landing switch in a variety of power loss and power return conditions. A method for operating the UPS based on an availability of power from a main power source is shown in FIG. 15.

In one example of the present disclosure, the imaging system may include a gantry. The gantry may include an X-ray tube bearing, such as a liquid bearing, which may be cooled following operation. To execute a cooling routine of the X-ray tube bearing in the gantry, power, such as electrical energy, may be consumed. In an event where power is not supplied to the imaging system, shutdown of the gantry power may occur without cooling the bearing, which may result in degradation and/or a reduced useful life.

In many applications, the imaging system may be arranged proximate to a UPS system configured to provide back-up power to a computer and a console of the imaging system. However, the UPS system is not wired to provide power to the gantry to enable a desired cooling prior to shut down in the event where a main power source is interrupted (e.g., absent). Furthermore, the gantry may not be sized to power the computer, the console, and the gantry for an extended period of time.

The inventors have recognized these drawbacks and come up with ways to adjust one or more electrical circuits between the UPS and the PDU to supply power from the UPS to the gantry when the main power source is unavailable. By doing this, an extra power source apart from the pre-existing UPS is not needed, which may decrease manufacturing and installation costs while also decreasing a packaging size of the system. For example, by adding multiple contactors (e.g., switches), a source of the power supply may be reliably controlled such that both supplies (e.g., the UPS and the main power source) are not providing power simultaneously.

FIGS. 1 to 14 show example configurations with relative positioning of the various components. If shown directly contacting each other, or directly coupled, then such elements may be referred to as directly contacting or directly coupled, respectively, at least in one example. Similarly, elements shown contiguous or adjacent to one another may be contiguous or adjacent to each other, respectively, at least in one example. As an example, components laying in face-sharing contact with each other may be referred to as in face-sharing contact. As another example, elements positioned apart from each other with only a space therebetween and no other components may be referred to as such, in at least one example. As yet another example, elements shown above/below one another, at opposite sides to one another, or to the left/right of one another may be referred to as such, relative to one another. Further, as shown in the figures, a topmost element or point of element may be referred to as a "top" of the component and a bottommost element or point of the element may be referred to as a "bottom" of the component, in at least one example. As used herein, top/bottom, upper/lower, above/below, may be relative to a vertical axis of the figures and used to describe positioning of elements of the figures relative to one another. As such, elements shown above other elements are positioned vertically above the other elements, in one example. As yet another example, shapes of the elements depicted within the figures may be referred to as having those shapes (e.g., such as being circular, straight, planar, curved, rounded, chamfered, angled, or the like). Further, elements shown intersecting one another may be referred to as intersecting elements or intersecting one another, in at least one example. Further still, an element shown within another element or shown outside of another element may be referred as such, in one example.

Though a CT imaging system is described by way of example, it should be understood that the present methods and systems may also be useful when applied to other imaging systems, such as X-ray imaging systems, magnetic resonance imaging (MRI) systems, positron emission tomography (PET) imaging systems, single-photon emission computed tomography (SPECT) imaging systems, ultrasound imaging systems, and combinations thereof (e.g., multi-modality imaging systems, such as PET/CT, PET/MR or SPECT/CT imaging systems). The present discussion of a CT imaging system is provided merely as an example of one suitable imaging system.

FIG. 1 illustrates an exemplary CT imaging system 100 configured for CT imaging. Particularly, the CT imaging system 100 is configured to image a subject such as a patient, an inanimate object, one or more manufactured parts, and/or foreign objects such as dental implants, stents, and/or contrast agents present within the body. In one embodiment, the CT imaging system 100 includes a gantry 108, which in turn, may further include at least one X-ray source 104 configured to project a beam of X-ray radiation 106 (see FIG. 2). Specifically, the X-ray source 104 is configured to project the X-ray radiation beams 106 towards an X-ray detector array 108 positioned on the opposite side of the gantry 108. Although FIG. 1 depicts only a single X-ray source 104, in certain embodiments, multiple X-ray sources and detectors may be employed to project a plurality of X-ray radiation beams 106 for acquiring projection data at different energy levels corresponding to the patient. In some embodiments, the X-ray source 104 may enable dual-energy gemstone spectral imaging (GSI) by rapid peak kilovoltage (kVp) switching. In some embodiments, the X-ray detector employed is a photon-counting detector which is capable of differentiating X-ray photons of different energies. In other embodiments, two sets of X-ray sources and detectors are used to generate dual-energy projections, with one set at low-kVp and the other at high-kVp. It should thus be appreciated that the methods described herein may be implemented with single energy acquisition techniques as well as dual energy acquisition techniques.

In certain embodiments, the CT imaging system 100 further includes an image processor 110 configured to reconstruct images of a target volume of the subject using an iterative or analytic image reconstruction method. For example, the image processor 110 may use an analytic image reconstruction approach such as filtered back projection (FBP) to reconstruct images of a target volume of the patient. As another example, the image processor 110 may use an iterative image reconstruction approach such as advanced statistical iterative reconstruction (ASIR), conjugate gradient (CG), maximum likelihood expectation maximization (MLEM), model-based iterative reconstruction (MBIR), and so on to reconstruct images of a target volume of the subject. As described further herein, in some examples the image processor 110 may use both an analytic image reconstruction approach such as FBP in addition to an iterative image reconstruction approach.

In some CT imaging system configurations, an X-ray source projects a cone-shaped X-ray radiation beam which is collimated to lie within an X-Y-Z plane of a Cartesian coordinate system and generally referred to as an "imaging plane." The X-ray radiation beam passes through an object being imaged, such as the patient or subject. The X-ray radiation beam, after being attenuated by the object, impinges upon an array of detector elements. The intensity of the attenuated X-ray radiation beam received at the detector array is dependent upon the attenuation of an X-ray radiation beam by the object. Each detector element of the array produces a separate electrical signal that is a measurement of the X-ray beam attenuation at the detector location. The attenuation measurements from all the detector elements are acquired separately to produce a transmission profile.

In some CT imaging systems, the X-ray source and the detector array are rotated with a gantry within the imaging plane and around the object to be imaged such that an angle at which the X-ray radiation beam intersects the object constantly changes. A group of X-ray radiation attenuation measurements, e.g., projection data, from the detector array at one gantry angle is referred to as a "view." A "scan" of the object includes a set of views made at different gantry angles, or view angles, during one revolution of the X-ray source and detector.

The projection data is processed to reconstruct an image that corresponds to a two-dimensional slice taken through the object or, in some examples where the projection data includes multiple views or scans, a three-dimensional rendering of the object. One method for reconstructing an image from a set of projection data is referred to in the art as the filtered back projection technique. Transmission and emission tomography reconstruction techniques also include statistical iterative methods such as maximum likelihood expectation maximization (MLEM) and ordered-subsets expectation-reconstruction techniques as well as iterative reconstruction techniques. This process converts the attenuation measurements from a scan into integers called "CT numbers" or "Hounsfield units," which are used to control the brightness of a corresponding pixel on a display device.

To reduce the total scan time, a "helical" scan may be performed. To perform a "helical" scan, the patient is moved while the data for the prescribed number of slices is acquired. Such a system generates a single helix from a cone beam helical scan. The helix mapped out by the cone beam yields projection data from which images in each prescribed slice may be reconstructed.

As used herein, the phrase "reconstructing an image" is not intended to exclude embodiments of the present invention in which data representing an image is generated but a viewable image is not. Therefore, as used herein, the term "image" broadly refers to both viewable images and data representing a viewable image. However, many embodiments generate (or are configured to generate) at least one viewable image.

The CT imaging system 100 may receive power from a main power source 122 or from an uninterruptible power source (UPS) 124 through a power distribution unit (PDU) 120. Additionally or alternatively, the CT imaging system may receive power from a generator, wherein power from the generator may be provided through a similar coupling as the main power source 122. In one example, the PDU 120 may include one or more sensors configured to sense an availability of power from the main power source 122. A PDU controller 130 may be configured to receive feedback from the plurality of sensors and adjust a position of one or more actuators in response to the availability of power from the main power source 122 as well as command signals from a gantry control board (GCB) in the CT imaging system 102. The one or more actuators may be adjusted after a specified time delay is measured by a timer. In one example, the one or more actuators are contactors and/or switches, configured to alternate between the main power source 122 and the UPS 124 based on the availability of power from the main power source 122. In one example, if power from the main power source is unavailable, then the PDU controller 130 may signal to actuate a first switch to break a circuit in which the main power source 122 is arranged and to actuate a second switch to complete a circuit in which the UPS 124 is arranged such that power is supplied from the UPS 124 to the CT imaging system, as will be described in greater detail below.

The PDU controller 130 may include instructions stored on memory thereof that when executed cause the PDU controller 130 to adjust switches or contactors controlling power received from the main power source 122 when power from the main power source is unavailable. Power from the main power source 122 may be detected via a current sensor. Feedback from the current sensor may prompt the PDU controller 130 to actuate switches from the main power source 122 while actuating a UPS switch (after a time delay) from the UPS to output loads of the PDU 120 to power the CT imaging system 100.

FIG. 2 illustrates an exemplary imaging system 200 similar to the CT imaging system 100 of FIG. 1. In accordance with aspects of the present disclosure, the imaging system 200 is configured for imaging a subject 204. In one embodiment, the imaging system 200 includes the detector array 108 (see FIG. 1). The detector array 108 further includes a plurality of detector elements 202 that together sense the X-ray radiation beam 106 (see FIG. 2) that pass through the subject 204 (such as a patient) to acquire corresponding projection data. Accordingly, in one embodiment, the detector array 108 is fabricated in a multi-slice configuration including the plurality of rows of cells or detector elements 202. In such a configuration, one or more additional rows of the detector elements 202 are arranged in a parallel configuration for acquiring the projection data.

In certain embodiments, the imaging system 200 is configured to traverse different angular positions around the subject 204 for acquiring desired projection data. Accordingly, the gantry 108 and the components mounted thereon may be configured to rotate about a center of rotation 206 for acquiring the projection data, for example, at different energy levels. Alternatively, in embodiments where a projection angle relative to the subject 204 varies as a function of time, the mounted components may be configured to move along a general curve rather than along a segment of a circle.

As the X-ray source 104 and the detector array 108 rotate, the detector array 108 collects data of the attenuated X-ray beams. The data collected by the detector array 108 under-goes pre-processing and calibration to condition the data to represent the line integrals of the attenuation coefficients of the scanned subject 204. The processed data are commonly called projections.

In some examples, the individual detectors or detector elements 202 of the detector array 108 may include photon-counting detectors which register the interactions of individual photons into one or more energy bins. It should be appreciated that the methods described herein may also be implemented with energy-integrating detectors.

The acquired sets of projection data may be used for basis material decomposition (BMD). During BMD, the measured projections are converted to a set of material-density projections. The material-density projections may be reconstructed to form a pair or a set of material-density map or image of each respective basis material, such as bone, soft tissue, and/or contrast agent maps. The density maps or images may be, in turn, associated to form a volume rendering of the basis material, for example, bone, soft tissue, and/or contrast agent, in the imaged volume.

Once reconstructed, the basis material image produced by the imaging system 200 reveals internal features of the subject 204, expressed in the densities of two basis materials. The density image may be displayed to show these features. In traditional approaches to diagnosis of medical conditions, such as disease states, and more generally of medical events, a radiologist or physician would consider a hard copy or display of the density image to discern characteristic features of interest. Such features might include lesions, sizes and shapes of particular anatomies or organs, and other features that would be discernable in the image based upon the skill and knowledge of the individual practitioner.

In one embodiment, the imaging system 200 includes a control mechanism 208 to control movement of the components such as rotation of the gantry 108 and the operation of the X-ray source 104. In some embodiments, the control mechanism includes a timer 209. In certain embodiments, the control mechanism 208 further includes an X-ray controller 210 configured to provide power and timing signals to the X-ray source 104. Additionally, the control mechanism 208 includes a gantry motor controller 212 configured to control a rotational speed and/or position of the gantry 108 based on imaging requirements.

In certain embodiments, the control mechanism 208 further includes a data acquisition system (DAS) 214 configured to sample analog data received from the detector elements 202 and convert the analog data to digital signals for subsequent processing. The DAS 214 may be further configured to selectively aggregate analog data from a subset of the detector elements 202 into so-called macro-detectors, as described further herein. The data sampled and digitized by the DAS 214 is transmitted to a computer or computing device 216. In one example, the computing device 216 stores the data in a storage device or mass storage 218. The storage device 218, for example, may include a hard disk drive, a floppy disk drive, a compact disk-read/write (CD-R/W) drive, a Digital Versatile Disc (DVD) drive, a flash drive, and/or a solid-state storage drive.

Additionally, the computing device 216 provides commands and parameters to one or more of the DAS 214, the X-ray controller 210, and the gantry motor controller 212 for controlling system operations such as data acquisition and/or processing. In certain embodiments, the computing device 216 controls system operations based on operator input. The computing device 216 receives the operator input, for example, including commands and/or scanning parameters via an operator console 220 operatively coupled to the computing device 216. The operator console 220 may include a keyboard (not shown) or a touchscreen to allow the operator to specify the commands and/or scanning parameters.

Although FIG. 2 illustrates only one operator console 220, more than one operator console may be coupled to the imaging system 200, for example, for inputting or outputting system parameters, requesting examinations, plotting data, and/or viewing images. Further, in certain embodiments, the imaging system 200 may be coupled to multiple displays, printers, workstations, and/or similar devices located either locally or remotely, for example, within an institution or hospital, or in an entirely different location via one or more configurable wired and/or wireless networks such as the Internet and/or virtual private networks, wireless telephone networks, wireless local area networks, wired local area networks, wireless wide area networks, wired wide area networks, etc.

In one embodiment, for example, the imaging system 200 either includes, or is coupled to, a picture archiving and communications system (PACS) 224. In an exemplary implementation, the PACS 224 is further coupled to a remote system such as a radiology department information system, hospital information system, and/or to an internal or external network (not shown) to allow operators at different locations to supply commands and parameters and/or gain access to the image data.

The computing device 216 uses the operator-supplied and/or system-defined commands and parameters to operate a table motor controller 226, which in turn, may control a table 114 which may be a motorized table. Specifically, the table motor controller 226 may move the table 114 for appropriately positioning the subject 204 in the gantry 108 for acquiring projection data corresponding to the target volume of the subject 204.

As previously noted, the DAS 214 samples and digitizes the projection data acquired by the detector elements 202. Subsequently, an image reconstructor 230 uses the sampled and digitized X-ray data to perform high-speed reconstruction. Although FIG. 2 illustrates the image reconstructor 230 as a separate entity, in certain embodiments, the image reconstructor 230 may form part of the computing device 216. Alternatively, the image reconstructor 230 may be absent from the imaging system 200 and instead the computing device 216 may perform one or more functions of the image reconstructor 230. Moreover, the image reconstructor 230 may be located locally or remotely, and may be operatively connected to the imaging system 200 using a wired or wireless network. Particularly, one exemplary embodiment may use computing resources in a "cloud" network cluster for the image reconstructor 230.

In one embodiment, the image reconstructor 230 stores the images reconstructed in the storage device 218. Alternatively, the image reconstructor 230 may transmit the reconstructed images to the computing device 216 for generating useful patient information for diagnosis and evaluation. In certain embodiments, the computing device 216 may transmit the reconstructed images and/or the patient information to a display or display device 232 communicatively coupled to the computing device 216 and/or the image reconstructor 230. In some embodiments, the reconstructed images may be transmitted from the computing device 216 or the image reconstructor 230 to the storage device 218 for short-term or long-term storage.

In one embodiment, the display 232 allows the operator to evaluate the imaged anatomy. The display 232 may also allow the operator to select a volume of interest (VOI) and/or request patient information, for example, via a graphical user interface (GUI) for a subsequent scan or processing.

In one example, the UPS 124 of FIG. 1 may be a preexisting UPS of the computing device 216 and auxiliary components thereof (e.g., the display 232, the operator console 220, etc.). As will be described herein, the inventors have found a way to modify one or more circuits of the PDU 120 and the UPS 124 of FIG. 1 such that the UPS 124 previously configured to only power the computing device 216 when the power from the main power source 122 was unavailable to also power the gantry 108. As such, a desired cooling of the gantry 108 may be executed in response to an event where power from the main power source 122 is unavailable.

Turning now to FIG. 3, it shows an embodiment 300 of a power interface of the UPS device 124 and the main power source 122 with the PDU 120. As such, components previously introduced may be similarly numbered in this figure and subsequent figures.

The power distribution unit 120 may include a circuit along which a breaker 302, a main power input contactor 304, and a transformer 305 having a primary winding 306, a first secondary winding 310 and a second secondary winding 330. The power distribution unit 120 may include a plurality of electrical lines 308 extending through corresponding switches in the main power input contactor 304 to the primary winding 306 of transformer 305. The breaker 302 may be configured to trip in response to 150 A (amps) or more of current flowing through any of the plurality of electric lines 308.

The primary winding 306 of transformer, which includes an electric winding configured to draw power from the plurality of electrical lines or wires 308. The winding may be electrically coupled to windings of a first secondary winding 310 and a second secondary winding 330. The main power input contactor 304 may be adjusted via a signal sent to an actuator thereof via a PDU controller (e.g., PDU controller 130 of FIG. 1) in response to power from the main power source 122 being absent. The main power input contactor 304 may be actuated to an open or a closed position, wherein the closed position completes the circuit and allows current to flow from the main power source 122 to the primary winding 306.

The first secondary winding 310, which may include a higher voltage than the second secondary winding 330, may direct power, via a plurality of electric wires 312, to a rectifier 316. The plurality of electrical lines or wires 312 may each include fuses 313 configured to disrupt the circuit in response to a current flow through the plurality of electrical lines or wires exceeding a rating of the fuses 313. A plurality of contacts (e.g., KXG contact 314, KSS contact 315) may be positioned between the fuses 313 and the rectifier 316. The rectifier 316 may be a passive or active rectifier, configured to convert alternating current (AC) to direct current (DC). The DC lines or wires are coupled to an output HVDC load 320, which may be used to supply power to a gantry (e.g., gantry 108 of FIG. 1). In one example, electrical power supplied to the output HVDC load 320 is a relatively high voltage (e.g., greater than 600V DC).

The second secondary winding 330, which may direct power, via a plurality of electrical lines or wires 332, to an output AC load 340. Each of the plurality of electrical lines or wires 332 may include a fuse, of a plurality of fuses 334, rated to disrupt the circuit in response to an electrical current exceeding a rating of the fuse. In one example, the fuses are rated to 50 A. However, the fuses may be rated to other amperages based on a sizing and amp rating of the plurality of electric wires 332. The output AC load 340 may send power to lower power demand devices, such as a console, power cabinet, computer, and the like.

The plurality of electrical lines or wires 332 may include a first splice 350 and a second splice 360. A plurality of first UPS electrical lines or wires 352 may be electrically coupled to the plurality of electrical lines or wires 332 at the first splice 350. A plurality of second UPS electrical lines or wires 362 may be electrically coupled to the plurality of electrical lines or wires 332 at the second splice 360. Each of the plurality of first and second UPS electrical lines or wires 352, 362 may be coupled to an interlocking switch 354. The interlocking switch 354 may be configured to adjust a position of a power-to position 356 and a power-from position 358 in tandem. Operation of the interlocking switch 354 in combination with the main power input contactor 304 is described in greater detail below.

The plurality of first and second UPS electrical lines or wires 352, 362 may be electrically coupled to a terminal block 364 and to input and output terminals of the UPS 124.

During normal operating conditions where the main power source 122 is active and providing power to the circuit, the main power input contactor 304 may be in a closed position. Power from the main power source 122 may be coupled to each of the output HVDC load 320, output AC load 340, and input of the UPS 124. Thus, the gantry and the console may be powered by the main power source 122. Furthermore, a state-of-charge (SOC) of the UPS 124 may be replenished. As such, the power-to position 356 of the interlocking switch 354 may be in a closed position. The power-from position 358, which corresponds to a position of the interlocking switch 354 configured to allow the UPS 124 to directly power the output HVDC load 320 and the output AC load 340 is in an open position (as illustrated in FIG. 3). Thus, power to the output AC load 340 is coupled through the plurality of electrical lines or wires 332, through the plurality of first UPS electrical lines or wires 352, through the UPS 124, through the plurality of second UPS electrical lines or wires 362, back to the plurality of electrical lines or wires 332, and to the output AC load 340. By opening the power from position 358, power from the UPS 124 may be blocked from the grid (e.g., the main power source 122). Herein, the power-to position 356 and the power-from position 358 may be interchangeably referred to as the power-to switch 356 and the power-from switch 358, respectively.

If power from the main power source 122 is interrupted and/or unavailable, then the main input contactor 304 and the power-to position 356 of the interlocking switch 354 are switched to open positions, via signals from the PDU controller to corresponding actuators and the power-from position 358 of the interlocking switch 354 is switched to a closed position. In one example, the interlocking switch 354, which may be mechanically or electronically controlled, may block the power-to and power-from positions to be open or closed simultaneously, thereby protecting circuits of the PDU 120. As such, the power-to switch and the power-from switch may be interlocked with one another. Thus, power from the UPS 124 may be coupled to the output AC load 340, as described above, and to the output HVDC load 320. Power from the UPS 124 may be coupled through the plurality of second UPS electrical lines or wires 362, through the closed power from switch 358, through the plurality of electrical lines or wires 332, and to the second secondary winding 330. The second secondary winding 330 may direct the power to the primary winding 306, which then increases a voltage of the power and directs it to the first secondary winding 310. The power from the first secondary winding 310 is converted from AC to DC at the rectifier 316, and then directed to the output HVDC load 320. By doing this, a preexisting UPS (e.g., UPS 124), originally sized to only power the output AC load 340 in response to the main power source 122 being unavailable, may be used to power the output HVDC load 320.

Turning now to FIG. 4A, it shows an embodiment of a control circuit 400 of the UPS (e.g., UPS 124 of FIGS. 1 and 3). FIG. 4B shows an embodiment of a control circuit 500 between the PDU (e.g., PDU 120 of FIGS. 1 and 3) and a gantry control board.

FIG. 4A shows the control circuit schematic 400 of the main circuit 300 which included main contactor 402 (or 304), forward 404 (or 356), reverse 406 (or 358), KXG 408 (or 314), KSS 409 (or 315) contactors and timer 412. Power-to position and power-from position are interchangeably referred to as forward contactor 404 (or 356) and reverse contactor 406 (or 358) herein. The coil 414 of main contactor 402 (or 304) is energized from main input power 122. The input power voltage 308 is 480V as an example. Two 2 A fuses 416 are positioned to protect the coil 414 for short circuit or over current. The coil 414 has electrical interlock with reverse contactor 406 (or 358) by using two contacts NC REV 405, which are closed when the utility power source is available, to ensure that the reverse contactor 406 (or 358) is not energized and there is no power from the UPS 124 to the second secondary winding 330.

The control circuit 400 includes two 120V input power source such as a first source 410 and a second source 411. It is possible to have both 120V power sources 410 and 411 providing power when the utility power source is available. The control circuit 400 may have only 120V input power from the first source 410 from UPS 124 during a power outage condition when the utility power source is unavailable. In another example, the control circuit 400 may have only 120V input power from the second source 411 from secondary winding 330 because the customer may not use UPS 124 for service or maintenance or the UPS is off at the first time powering. Therefore, a three-phase diode bridge 418 is used to allow the control circuit 400 to receive power at all three conditions.

The coil 420 of FWD contactor 404 (or 356) can be energized when the auxiliary contact 422 of the main contactor 402 (or 304) and the normally closed contact 424 of the REV contactor 406 (or 358) are closed in response to the utility power source being available. The coil of timer 412 is normally de-energized and may be energized in response to the utility power source being unavailable. The timer contactor 438 may then be closed after a pre-determined period to energize reverse coil 426 when the utility power source is unavailable. A contact 438 associated with the timer contactor 412 may be normally opened. The timer 412 is adjusted for 1 to 10 second as an example.

If the FWD contactor 404 (or 356) is closed, then the power from the secondary of winding 330 is coupled to the UPS 124 to charge the UPS batteries. This is a condition on the CT imaging system 100 where the utility power source is available.

The coil 426 of REV contactor 406 (or 358) can be energized when the normally open of the auxiliary contact of the KSS contactor 409 is closed and the FWD contactor 404 (or 358) is opened by closing the normally close contact 429 of the FWD contactor 404 (or 356). If the REV contactor 406 (or 358) is closed, then the power from the UPS 124 goes to the second secondary winding of transformer 330 and then transfer to the first secondary winding 310 and after rectifying by 316, the HVDC power will be available on output terminals 320. This may be a power outage case of CT imaging system 100. During a power outage where the utility power source is unavailable to the CT imaging system 100, there is an interlock circuit 430 between hardware and software CT imaging system 100 to protect the UPS 124 from an over-current or overload condition. The external interlock circuit 430 is in series with normally closed contact 432 of the REV contactor 406 (or 358). If the contact is opened then the CT imaging system is under power outage condition and the external interlock circuit 430 is opened. The missing signal of the external interlock circuit 430 goes to image processor 110 and then the CT imaging system 102 cannot scan. Therefore, the UPS 124 will be protected for overload condition.

FIG. 4B illustrates an embodiment 500 of the control circuit between the PDU 120 and the gantry control board. At first, the forward contact 502 and the reverse contact 504 are open. During the normal operation, the gantry control board sends a signal by closing the forward contact 502 to command the PDU 120 to close the KXG and KSS contacts 314, 315, with the KSS contact 315 being closed first. During power loss conditions, the gantry control board sends a signal by closing the reverse contact 504 to command the PDU 120 to close the KXG and KSS contacts 314, 315, with the KSS contact 315 being closed first.

Figure 5:
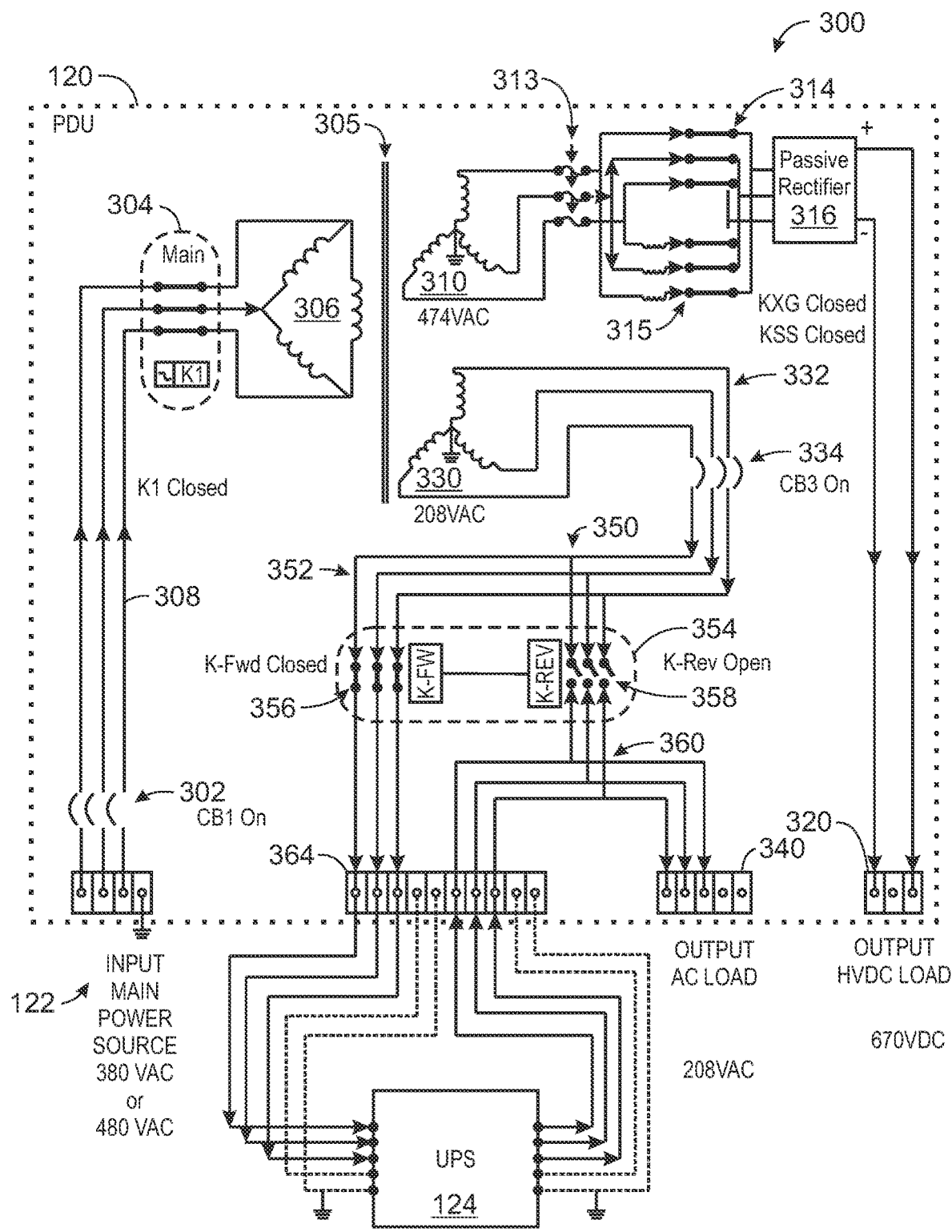
FIG. 5 shows a schematic diagram of the power circuitry of FIG. 3 under normal operating conditions.
Figure 6A:
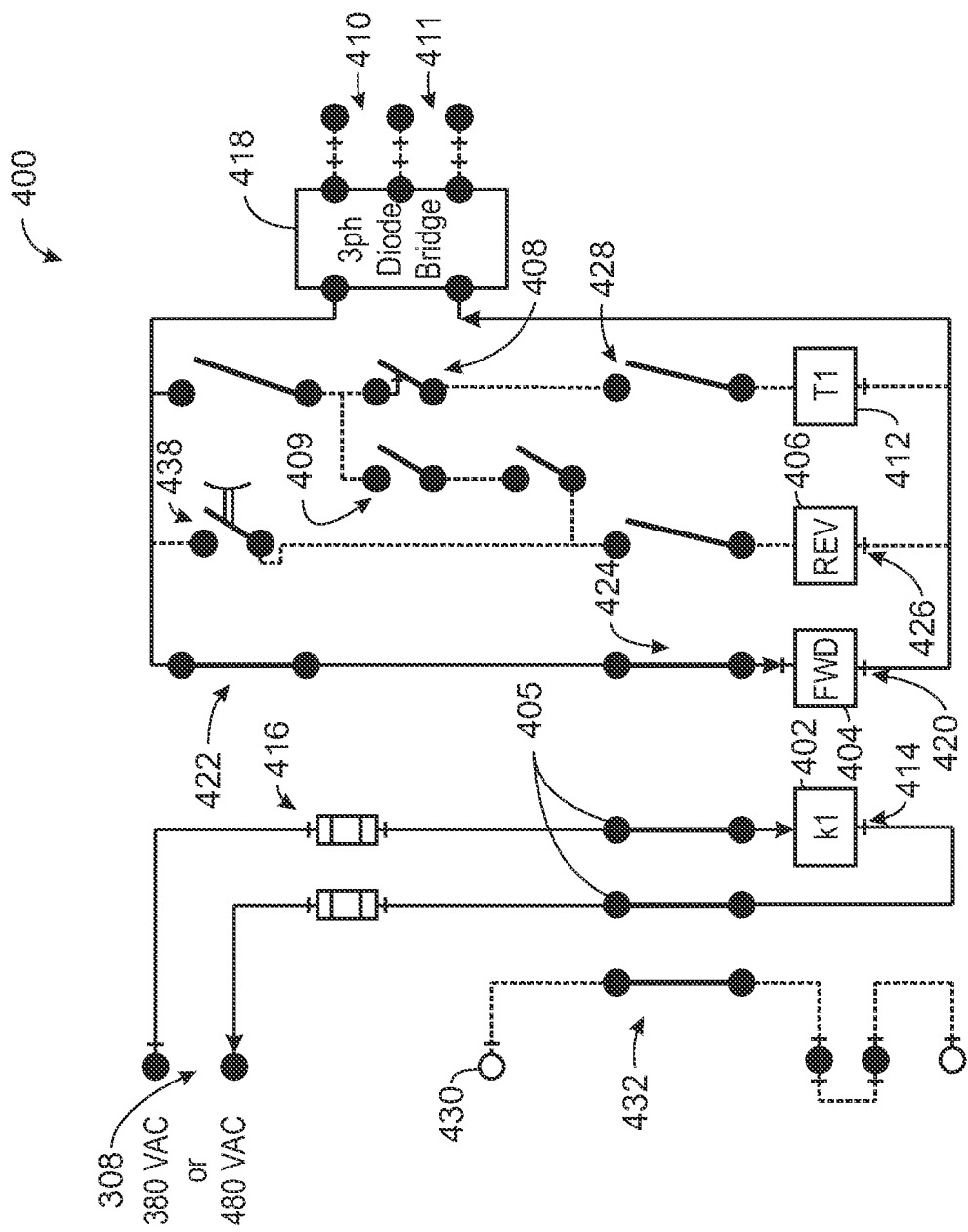
FIGS. 6A and 6B show schematic diagrams of the control circuitry of the power circuitry of FIG. 5 under normal operating conditions.
Figure 6B:
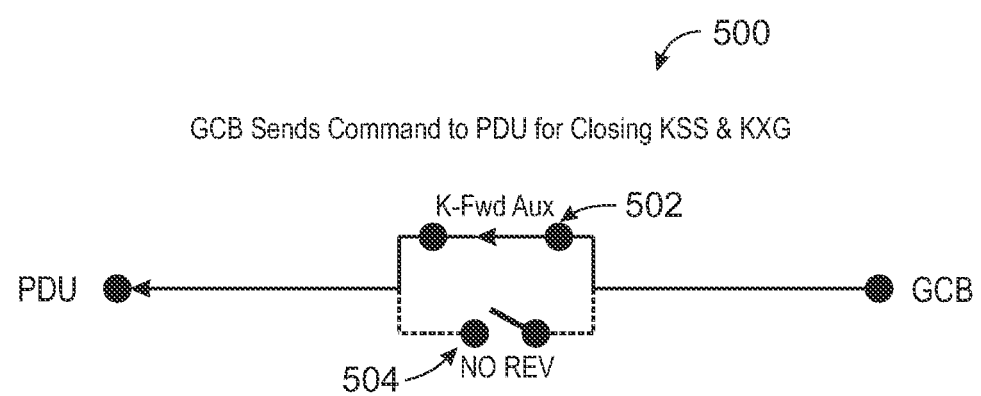

FIGS. 5-14B illustrate the example embodiment 300 in various stages during a loss of power from a main power source. FIG. 5 depicts the example embodiment 300 during normal operating conditions, where the main power source 122 is supplying power to the output HVDC load 320 via the first secondary winding 310 and rectifier 316. The main power source 122 is also providing power to the UPS 124 via the second secondary winding 330. The UPS 124 provides power to the output AC load 340. FIGS. 6A and 6B depict the control logic circuits 400 and 500 during normal operation. As shown in FIG. 6A, the main contactor 402 (or 304) is closed, the forward contactor 404 (or 356) is closed, the reverse contactor 406 (or 358) is opened, and the timer 412 is open. In FIG. 6B, the gantry control board provides a control signal to the PDU to close the KXG and KSS contacts 314, 315 when the auxiliary FWD contactor 502 is closed.

Figure 7:
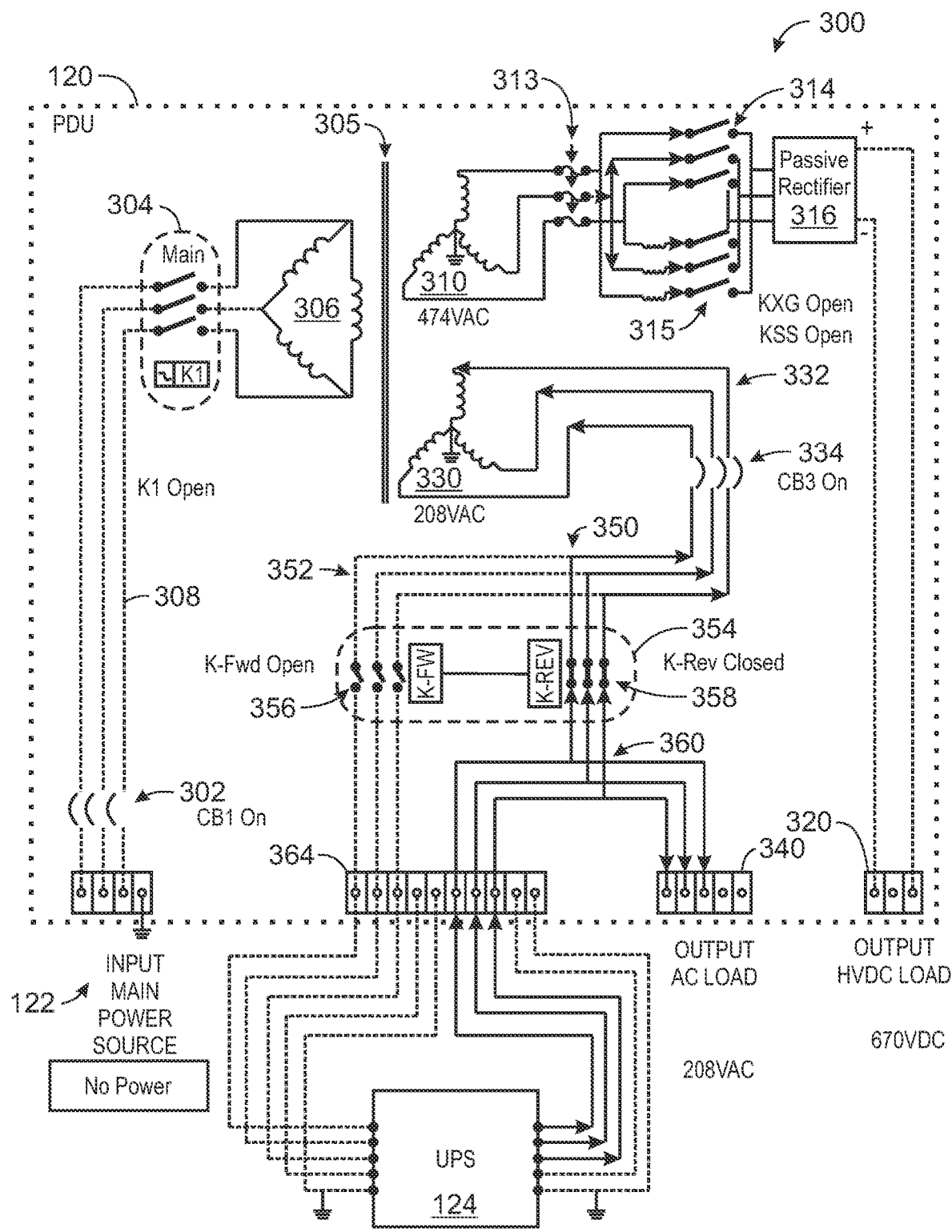
FIG. 7 shows a schematic diagram of the power circuitry of FIG. 3 under a first stage of power outage conditions.
Figure 8A:
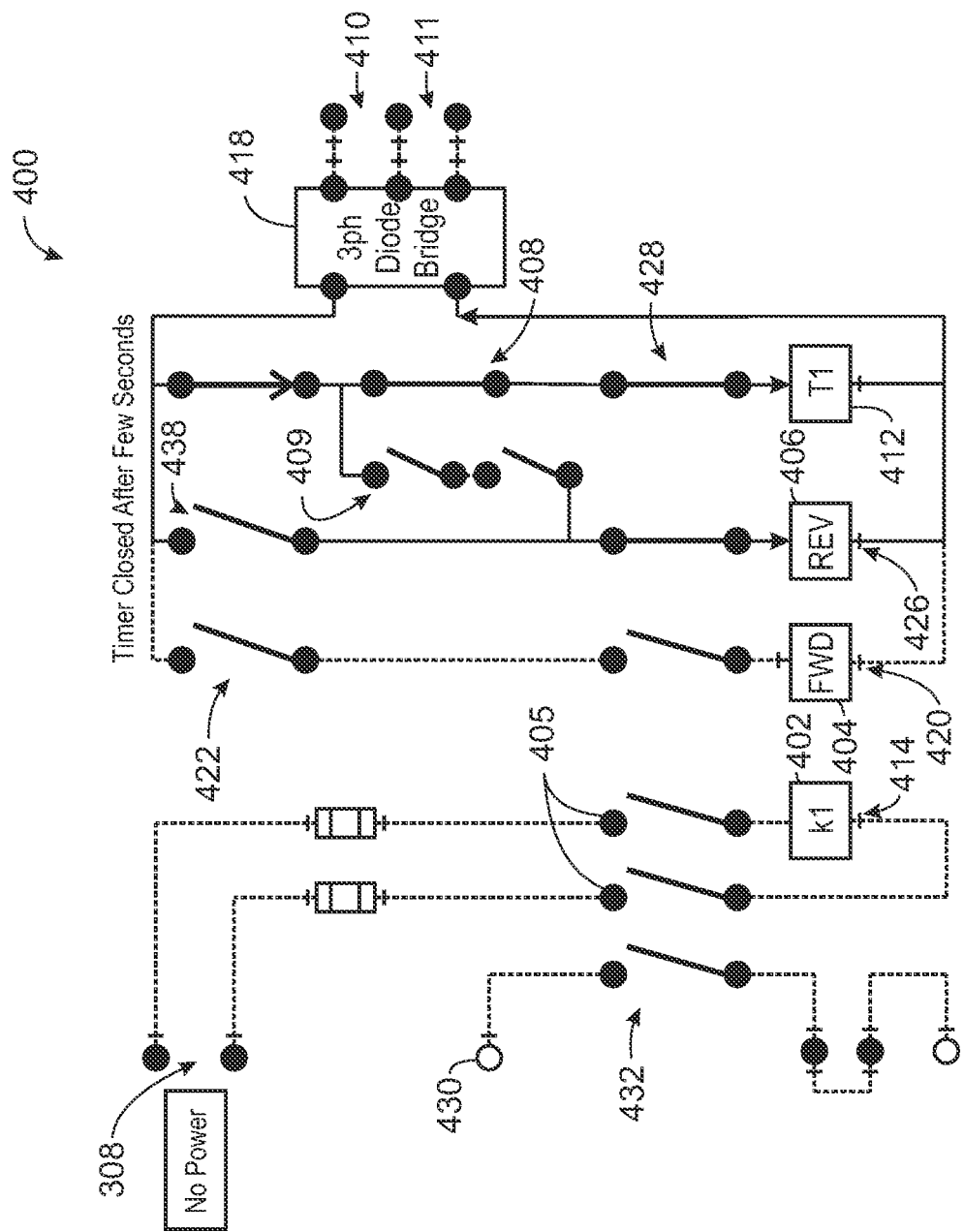
FIGS. 8A and 8B show schematic diagrams of the control circuitry of the power circuitry of FIG. 7 under the first stage of power outage conditions.
Figure 8B:
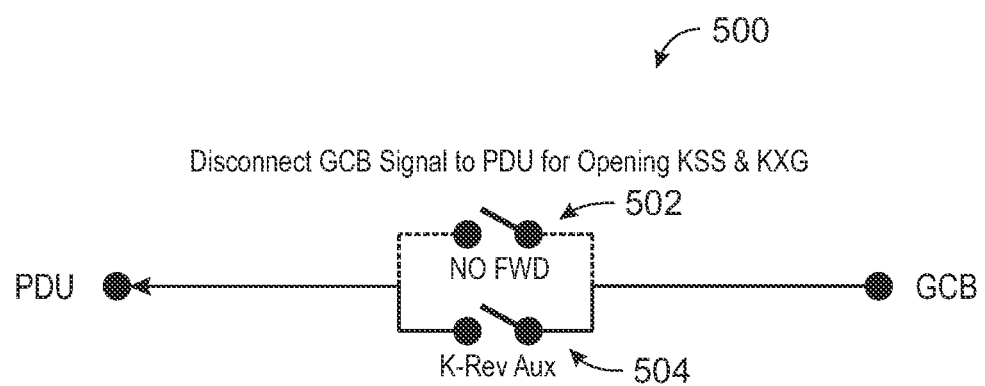

FIG. 7 depicts the example embodiment 300 during a first stage of the power loss or power outage conditions, where the main power source 122 is not supplying power. In the first stage of the power loss conditions, the KXG and KSS contacts 314, 315 were open as a result of the power loss and have not been closed yet. The interlocking switch 354 closes the REV contactor 358 after few delay time which is adjusted by timer 412 so that the UPS 124 can supply power to the second secondary winding 330, which powers the first secondary winding 310 via the primary winding 306. to the output HVDC load 320 via the first secondary winding 310 and rectifier 316. The UPS 124 is still providing power to the output AC load 340. FIGS. 8A and 8B depict the control logic circuits 400 and 500 initial power loss operation. As shown in FIG. 8A, the main contactor 402 (or 304) is open, the forward contactor 404 (or 356) is open, the reverse contactor 406 (or 358) is open, and the timer 412 is energized. The timing 412 turns on a timer 209 to begin counting until the time reaches a pre-determined threshold. In FIG. 8B, the gantry control board disconnects the control signal to the PDU for opening the KSS and KXG contactors 315, 314. After the timer 209 reaches the threshold, a timer's contact 438 is closed, which allows the reverse contactor 406 (or 358) to be energized. Energizing the reverse contactor 406 (or 358) enables to GCB signal to the PDU 120 for closing the KXG and KSS contacts 314, 315. The KXG and KSS 314, 315 contacts are open until after the signal from the GCB. The KSS contact 315 is closed first, then the KXG contact 314 is closed after approximately 1 second.

Figure 9:
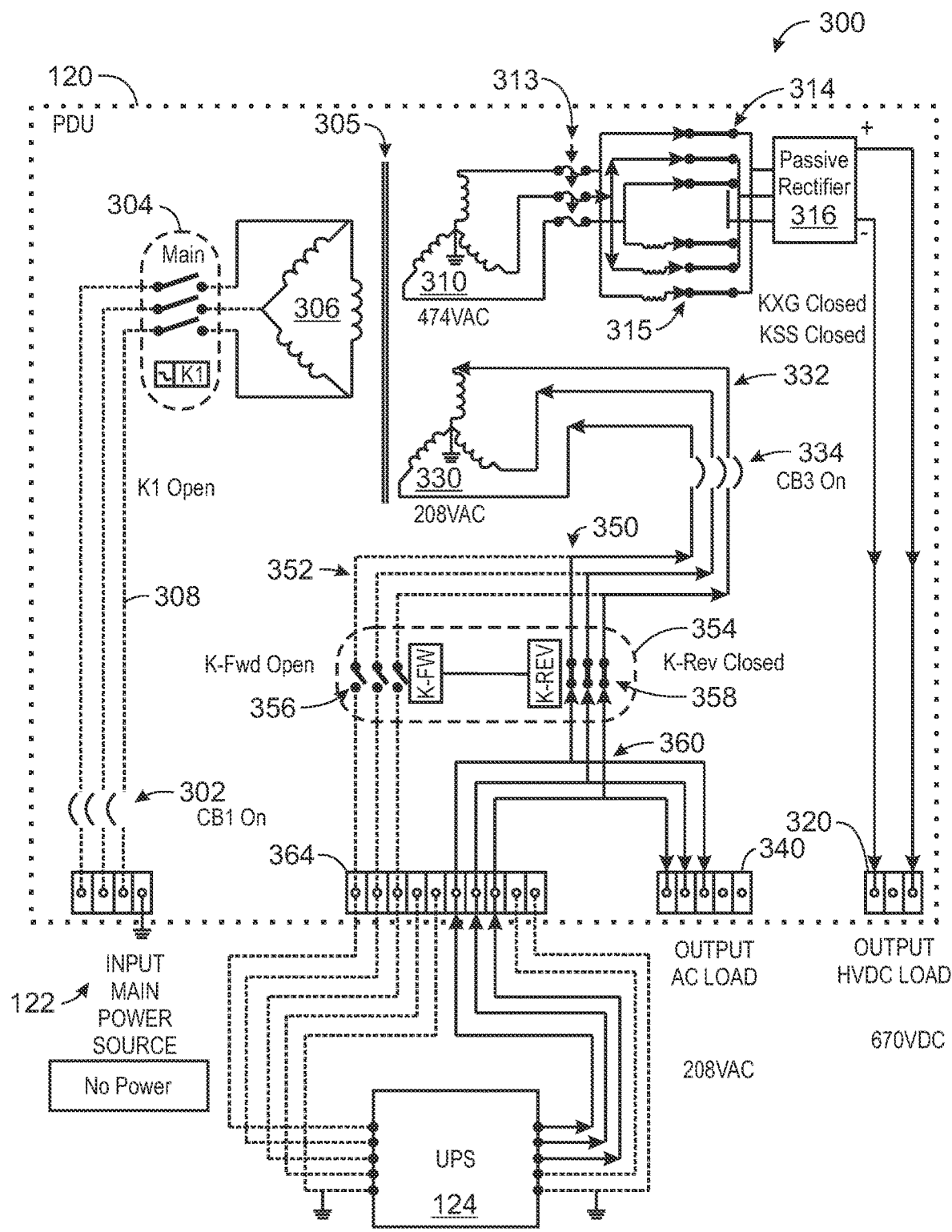
FIG. 9 shows a schematic diagram of the power circuitry of FIG. 7 under a second stage of power outage conditions after a time delay.
Figure 10A:
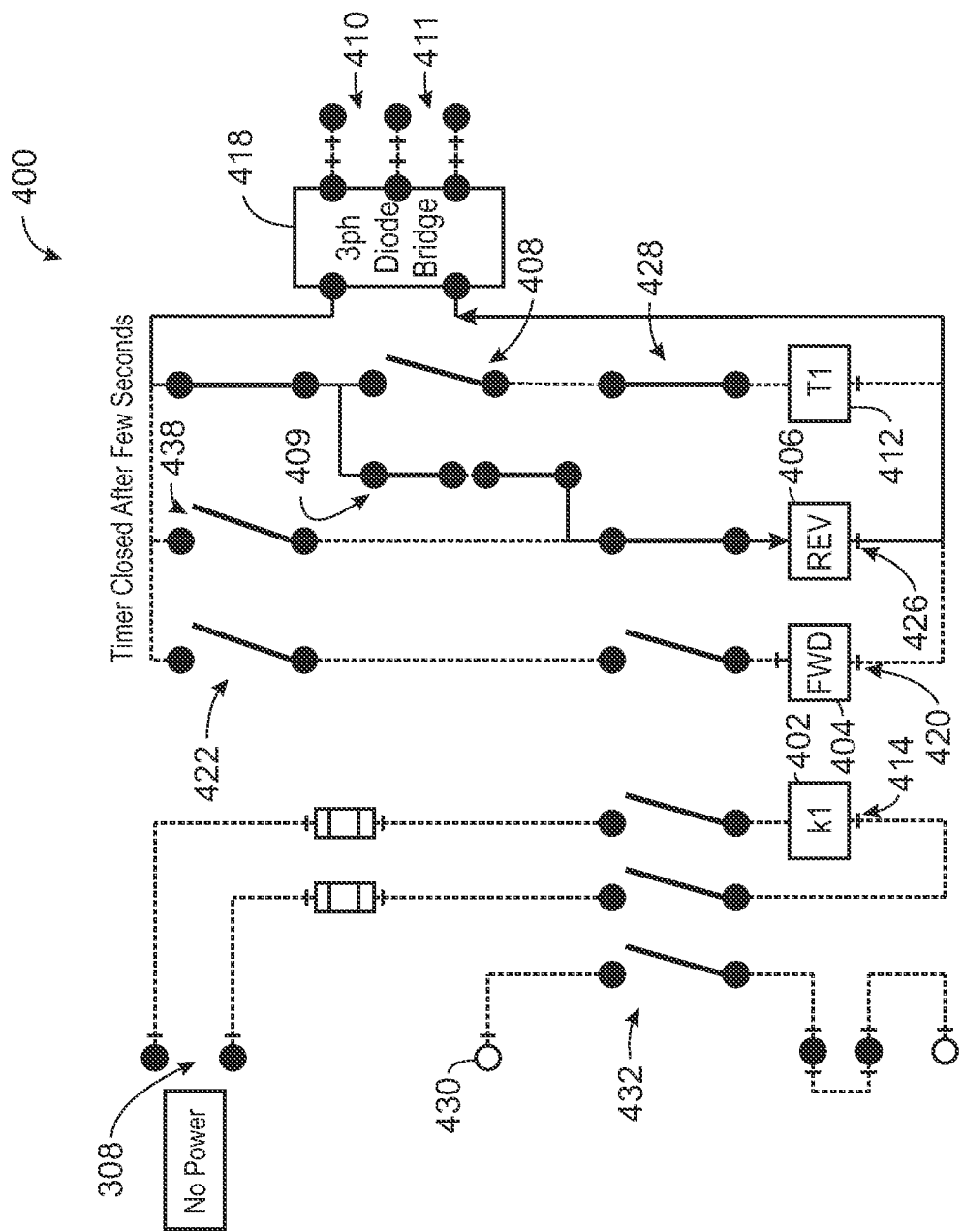
FIGS. 10A and 10B show schematic diagrams of the control circuitry of the power circuitry of FIG. 9 under the second stage of power outage conditions.
Figure 10B:
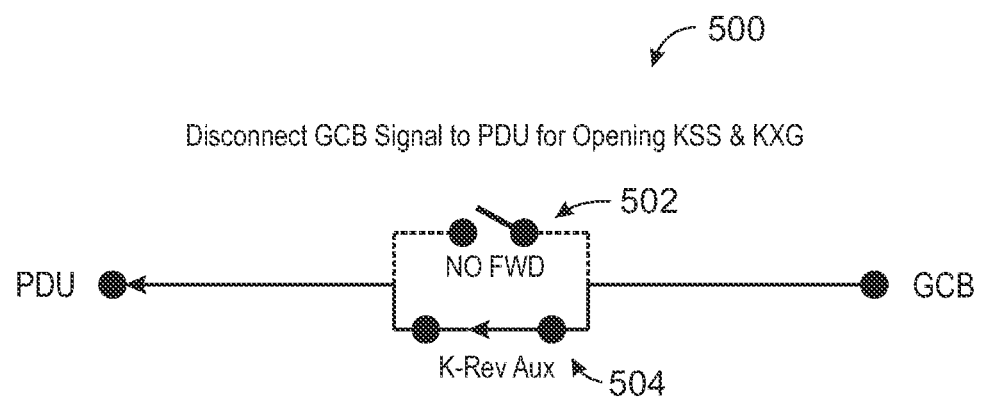

FIGS. 9-10B represent operation during a second stage of the power loss condition. During power loss operation, after the time has passed the threshold and the reverse contactor 406 (or 358) is energized, the UPS 124 is providing power to the output HVDC load 320 via the windings 306, 310, 330. The KSS and KXG contacts 314, 315 are still closed. The timer 209 also resets and the timer contact 438 opens, as shown in FIG. 10A. In some examples, such operation during a power loss condition may only continue as long as necessary to cool one or more components of the gantry 108, such as an X-ray tube. Alternatively, the power loss operation may continue until the main power source is restored. In some examples, the main power source is not restored while the UPS can provide power to the output HVDC load, so the gantry 108 is shut down completely.

Figure 11:
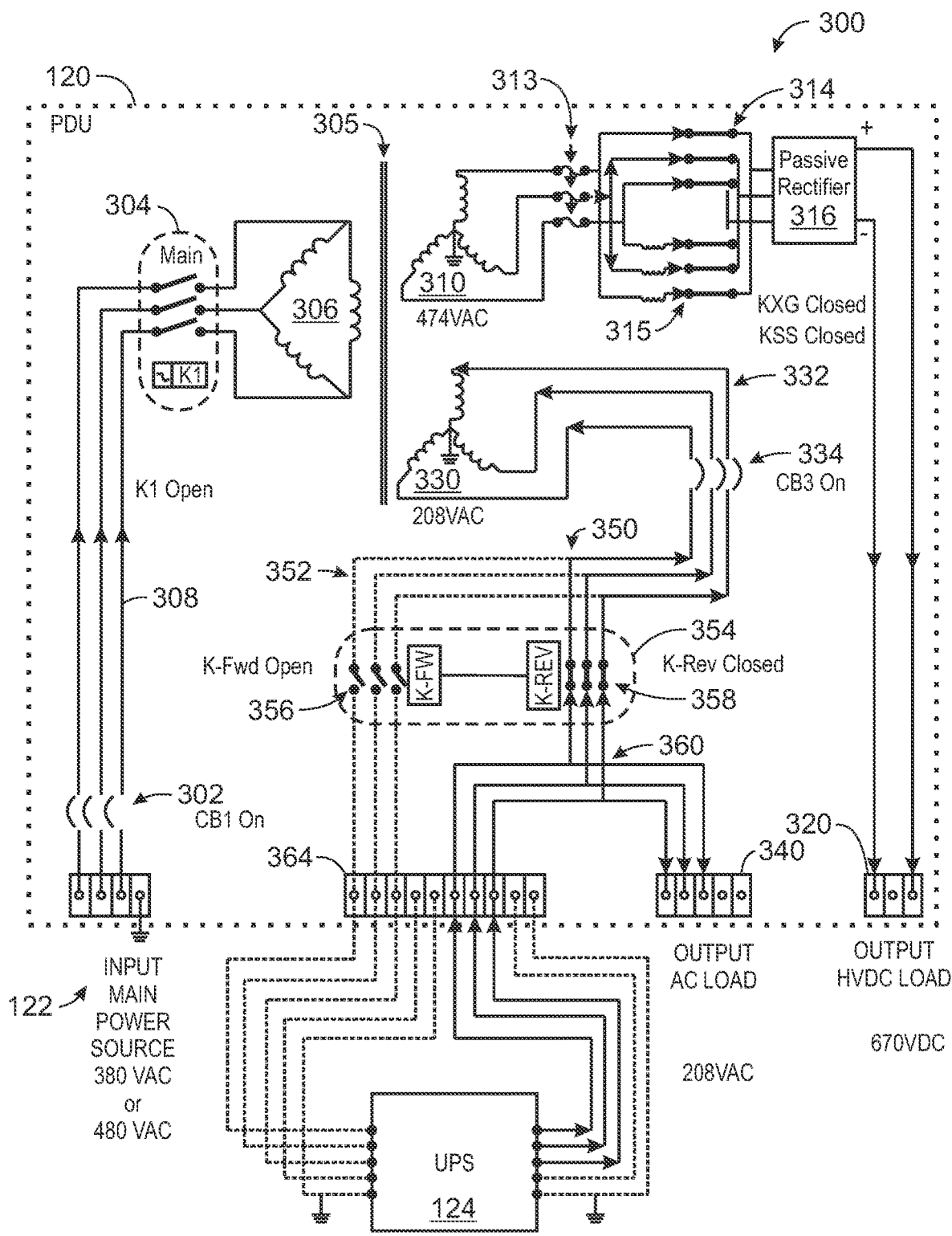
FIG. 11 shows a schematic diagram of the power circuitry of FIG. 9 under a third stage of power outage conditions when the main power source is returned.
Figure 12A:
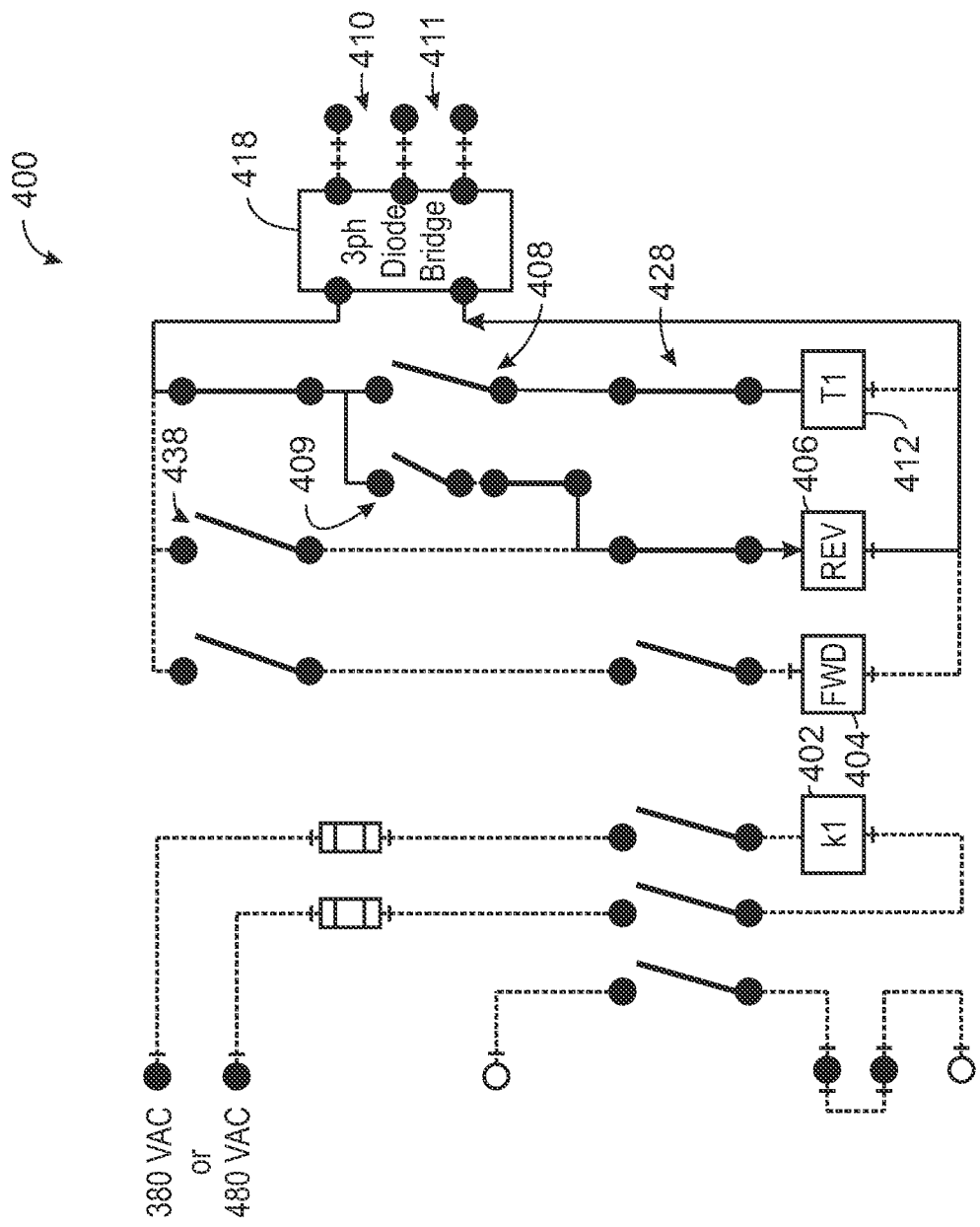
FIGS. 12A and 12B show schematic diagrams of the control circuitry of the power circuitry of FIG. 11 under the third stage of power outage conditions when the main power source is returned.
Figure 12B:
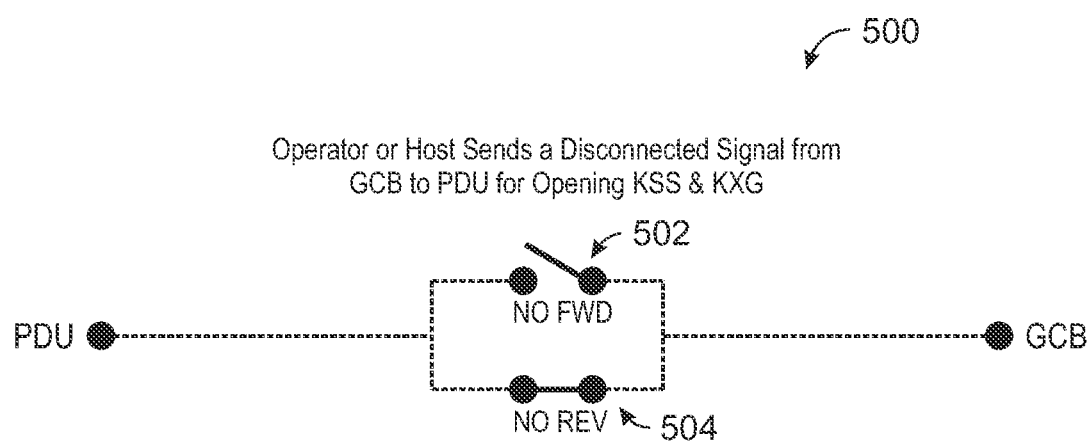
Figure 13:
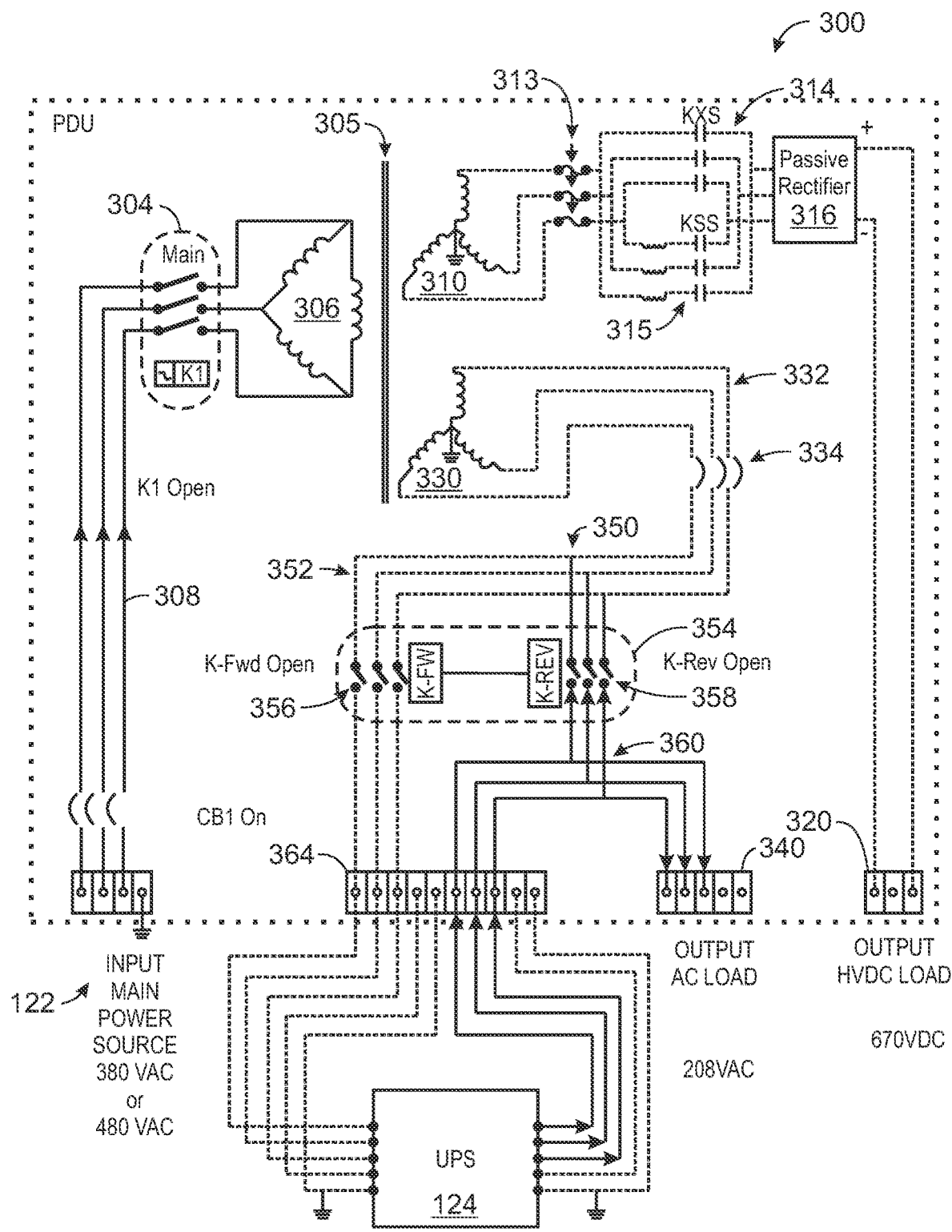
FIG. 13 shows a schematic diagram of the power circuitry of FIG. 11 during power transfer from the UPS to the main power source.
Figure 14A:
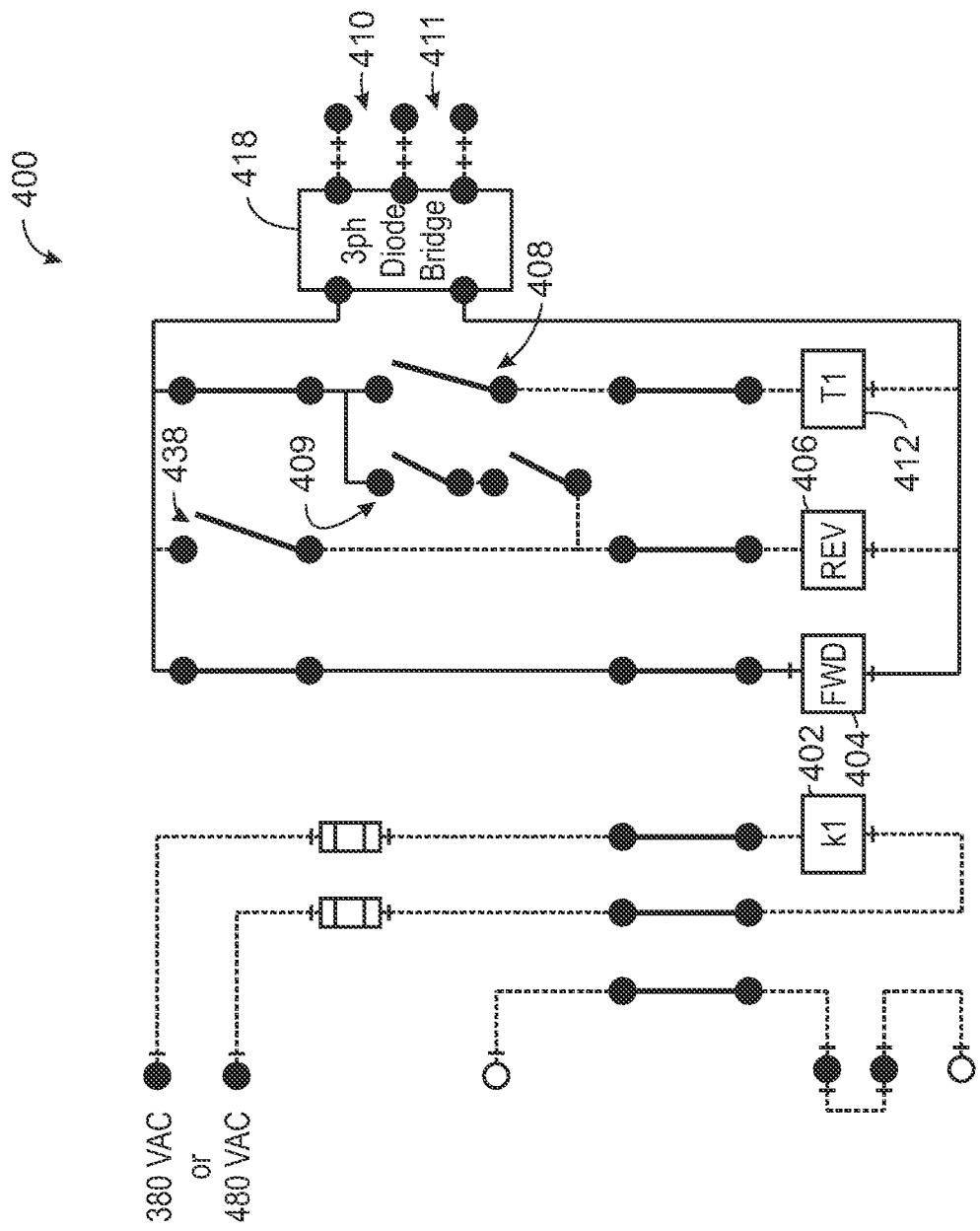
FIGS. 14A and 14B show schematic diagrams of the control circuitry of the power circuitry of FIG. 13 during power transfer from the UPS to the main power source.
Figure 14B:
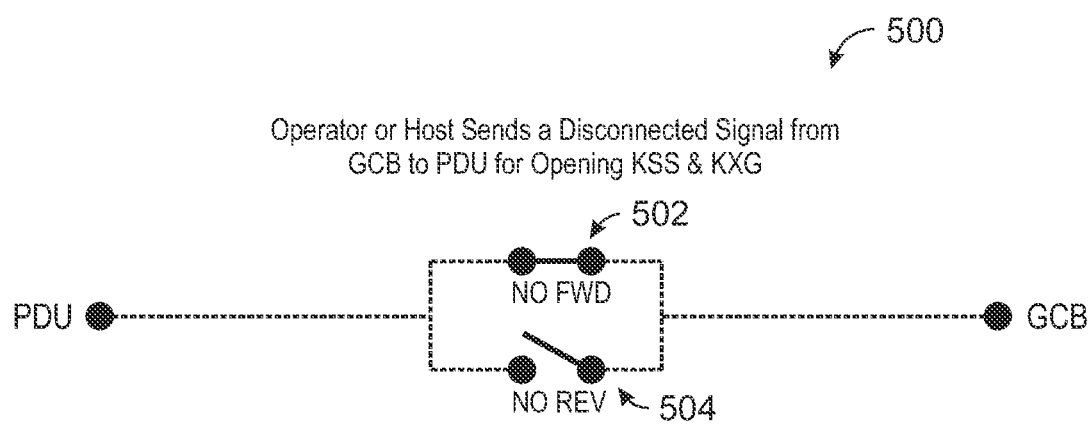
Figure 15:
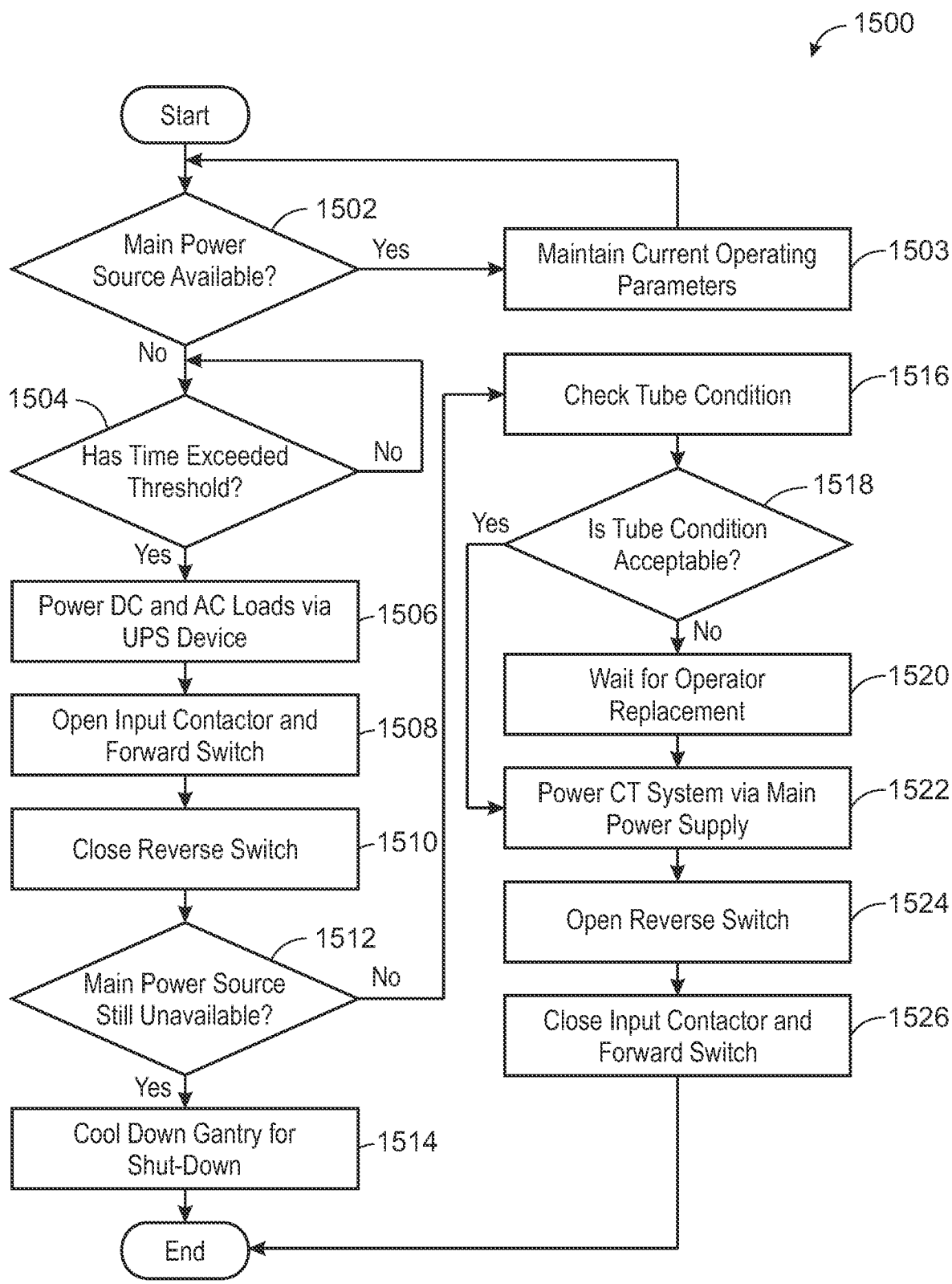
FIG. 15 shows a method for switching a power supply to the CT imaging system in response to an availability of power from the main power source and controlling return of the CT imaging system to the main power source.

FIGS. 11-14B depict a third stage of the power loss condition, or the power return conditions. When the main power source 122 is re-energized, the main contactor 304 does not immediately close, and the example embodiment 300 still continues operation as if the main power source 122 is unavailable, as shown in FIG. 11. The Kss and KXG contacts 314, 315 are closed. Components of the gantry 108, such as the X-ray tube, are evaluated for possible damage prior to opening the min contactor 304 and returning to normal operating conditions. If the components of the gantry 108 are not damaged and the tube and its Liquid Metal Bearing are cooled, the gantry control board sends a signal to the PDU to open the KXG and KSS contacts 314, 315 for less than a second and transfer the supply of power to the HVDC output load 320 from the UPS 124 to main power source 122, as shown in FIG. 12B. In some examples, an operator may provide the signal via the gantry control board. The KXG and KSS contacts are opened (FIG. 12A), thus de-energizing the reverse contactor 406 (or 358). The UPS 124 is no longer providing power to the output HVDC load 320. FIG. 13 depicts the system at this state, where no power is provided to the output HVDC load 320 because normal operating conditions are not yet resumed. FIGS. 14A and 14B depict the control logic at the end of the power return condition, just prior to the main contactor being closed. The KXG and KSS contacts 314, 315 are closed for less than a second and transfer the supply of power to the HVDC output load 320 from the UPS 124 to main power source 122. The main contactor 402 (or 304) is closed and normal operating conditions are restored, which are depicted in FIG. 5.

FIG. 15 depicts a method 1500 for adjusting an energy source based on an availability of electrical energy from a main power source. Instructions for the method may be executed by and stored on memory of a controller of the PDU (e.g., PDU controller 130 of FIG. 1). The controller may be configured to receive inputs from one or more sensors of the PDU and adjust operation of one or more switches to change the direction of current flow.

The method 1500 begins at 1502, which includes determining if a main power source is available and is above a threshold voltage. The threshold voltage may be 110 VAC or more. If the main power source is available, then the method 1500 may proceed to 1503, which includes maintaining current operating parameters. The voltage may be continuously or periodically checked to detect power source unavailability.

If the power source is not available, the method 1500 may proceed to 1504, which includes determining whether a time for which the power source has been unavailable has passed a threshold amount of time. In some examples, the threshold amount of time may be 10 seconds. Alternatively, the threshold may be between 1-10 seconds. After the amount of time passes the threshold, the method continues to 1506, which includes powering DC and AC loads via the UPS device. To power both the DC and AC loads using the UPS, the main contactor and forward contactor are opened at 1508, and the reverse switch is closed at 1510. In some examples, steps 1506, 1508, and 1510 may be performed in a different order, and/or substantially simultaneously.

The method 1500 continues by determining whether the main power source is still unavailable at 1512. In some examples, the UPS may provide power to the DC and AC loads for a designated amount of time, at which time it is determined whether the main power source is available. Alternatively, the UPS may continuously check for the main power source to become available. In some examples, if the main power source is available for an extended period of time, the UPS may not be able to provide power to the DC output any longer. For example, in response to a state-of-charge (SOC) of the UPS being less than a threshold SOC, the gantry enters shut-down mode. The threshold SOC is based on an amount of power used to cool a plurality of systems within the gantry during the shut-down mode. If the main power source is still unavailable at 1512, the method may proceed to 1514 by cooling the gantry for shut-down, and the method is complete. If the main power source is available, the method continues at 1516 by checking the condition of the gantry components, specifically the X-ray tube. If the tube condition is not acceptable at 1518, the method waits for an operator replacement at 1520. If the tube condition is acceptable at 1518, or after the operator replacement, the method continues at 1522 by powering the CT system via the main power source. The reverse switch is opened at 1524, then the main contactor and forward contactors are closed at 1526. The method is complete.

As used herein, an element or step recited in the singular and proceeded with the word "a" or "an" should be understood as not excluding plural of said elements or steps, unless such exclusion is explicitly stated. Furthermore, references to "one embodiment" of the invention do not exclude the existence of additional embodiments that also incorporate the recited features. Moreover, unless explicitly stated to the contrary, embodiments "comprising," "including," or "having" an element or a plurality of elements having a particular property may include additional such elements not having that property. The terms "including" and "in which" are used as the plain-language equivalents of the respective terms "comprising" and "wherein." Moreover, the terms "first," "second," and "third," etc. are used merely as labels, and are not intended to impose numerical requirements or a particular positional order on their objects.

The control methods and routines disclosed herein may be stored as executable instructions in non-transitory memory and may be carried out by the control system including the controller in combination with the various sensors, actuators, and other engine hardware. The specific routines described herein may represent one or more of any number of processing strategies such as event-driven, interrupt-driven, multi-tasking, multi-threading, and the like. As such, various actions, operations, and/or functions illustrated may be performed in the sequence illustrated, in parallel, or in some cases omitted. Likewise, the order of processing is not necessarily required to achieve the features and advantages of the example embodiments described herein, but is provided for ease of illustration and description. One or more of the illustrated actions, operations and/or functions may be repeatedly performed depending on the particular strategy being used. Further, the described actions, operations and/or functions may graphically represent code to be programmed into non-transitory memory of the computer readable storage medium in the engine control system, where the described actions are carried out by executing the instructions in a system including the various engine hardware components in combination with the electronic controller.

This written description uses examples to disclose the invention, including the best mode, and also to enable a person of ordinary skill in the relevant art to practice the invention, including making and using any devices or systems and performing any incorporated methods. The patentable scope of the invention is defined by the claims, and may include other examples that occur to those of ordinary skill in the art. Such other examples are intended to be within the scope of the claims if they have structural elements that do not differ from the literal language of the claims, or if they include equivalent structural elements with insubstantial differences from the literal languages of the claims.

The invention claimed is:

1. A system, comprising:
a power distribution unit (PDU) configured to receive power from a main power source and an uninterruptible power supply (UPS), wherein the UPS includes a timer and an interlocking switch, wherein the UPS is configured to directly power an output alternating current (AC) load after the main power source in unavailable, and the UPS is further configured to power an output high voltage direct current (HVDC) load after the main power source is unavailable for a time delay measured by the timer, wherein the interlocking switch is actuated after the delay to allow the UPS to directly power the output HVDC load, and wherein the interlocking switch allows power to either be provided to the UPS or supplied from the UPS; and
a transformer having a primary winding, a first secondary winding, and a second secondary winding, wherein the UPS is configured to power the output AC load, and power the output HVDC load after the time delay by providing power to the first secondary winding and the second secondary winding.

2. The system of claim 1, further comprising at least one contactor, wherein the at least one contactor is switched to couple the UPS to the first secondary winding, the second secondary winding, a rectifier, and the output HVDC load, wherein the rectifier converts the AC to HVDC.

3. The system of claim 2, further comprising a main input contactor, wherein the main input contactor is in an open position to disconnect power from the main power source to the primary winding.

4. The system of claim 1, wherein the output AC load supplies AC power to a plurality of systems of a computed tomography (CT) imaging system.

5. The system of claim 1, wherein the output HVDC load supplies HVDC power to a plurality of systems within a gantry of a computed tomography (CT) imaging system.

6. The system of claim 1, wherein the UPS is configured to power the output AC load and the output HVDC load in response to power from the main power source being unavailable.

7. A computed tomography (CT) imaging system, comprising:
a gantry coupled to an output HVDC load;
a power cabinet coupled to an output AC load;
a power distribution unit (PDU) comprising a transformer having a primary winding, a first secondary winding, and a second secondary winding;
wherein the PDU is configured to receive power from one of a main power source and an uninterruptible power supply (UPS);
a plurality of contactors, and interlocking switch which allows power to either be provided to the UPS or supplied from the UPS, and a timer coupled to the PDU and UPS; and
a controller with computer readable instructions stored on memory thereof for controlling the plurality of contactors based on availability of the main power source and an input from the timer, wherein power is coupled from the UPS to the output HVDC load by actuating the interlocking switch after the main power source is unavailable for a time delay measured by the timer, and wherein the UPS is configured to power the output AC load, and power the output HVDC load after the time delay by providing power to the first secondary winding and the second secondary winding.

8. The CT imaging system of claim 7, wherein the gantry enters a shut-down mode in response to a state-of-charge (SOC) of the UPS being less than a threshold SOC, wherein the threshold SOC is based on an amount of power used to cool a plurality of systems within the gantry during the shut-down mode.

9. The CT imaging system of claim 7, wherein power is coupled directly from the UPS to the output AC load.

10. The CT imaging system of claim 7, wherein a voltage provided to the first secondary winding by the UPS is less than a voltage of the second secondary winding.

11. The CT imaging system of claim 7, wherein the instructions further enable the controller to adjust the position of the plurality of contactors to open positions and closed positions in response to power from the main power source being available and an input from the timer.

12. The CT imaging system of claim 7, wherein the plurality of contactors may be independently controlled contactors.

13. A method for a computed tomography (CT) imaging system, the method executed via instructions stored on memory of a controller, the method, comprising:
in response to a main power source being unavailable;
powering an output AC load directly via an uninterruptible power supply (UPS);
waiting for a time delay;
actuating an interlocking switch thereby powering an output HVDC load via power coupled from the UPS to a first secondary winding of a transformer, a primary winding of the transformer, a second secondary winding of the transformer, and through a rectifier, wherein the interlocking switch allows power to either be provided to the UPS or supplied from the UPS; and
in response to the main power source becoming available:
determining an X-ray tube condition; and
powering the output HVDC load via the main power source.

14. The method of claim 13, further comprising adjusting a position of a main contactor to an open position to disconnect the primary transformer from the main power source.

15. The method of claim 14, further comprising adjusting a position of a reverse switch to a closed position to couple the UPS to the first secondary winding and a position of a forward contactor to an open position to block power from returning to the UPS.

16. The method of claim 13, further comprising powering a plurality of systems of the CT imaging system via the output AC load and powering a plurality of systems within a gantry of the CT imaging system via the output HVDC load.

17. The method of claim 16, further comprising cooling the plurality of systems within the gantry in response to the UPS powering the output HVDC load or a state-of-charge (SOC) of the UPS being less than a threshold SOC.

* * * * *